(12) United States Patent
Rimm et al.

(10) Patent No.: US 7,709,222 B2
(45) Date of Patent: May 4, 2010

(54) METHODS FOR MAKING CANCER PROGNOSES BASED ON SUBCELLULAR LOCALIZATION OF BIOMARKERS

(75) Inventors: David L. Rimm, Bradford, CT (US); Gregory Tedeschi, Cromwell, CT (US); Robert L. Camp, Stamford, CT (US); Mark Gustavson, Niantic, CT (US)

(73) Assignees: Yale University, New Haven, CT (US); Historx, Inc., New Haven, CT (US)

(*) Notice: Subject to any disclaimer, the term of this patent is extended or adjusted under 35 U.S.C. 154(b) by 0 days.

(21) Appl. No.: 11/827,694

(22) Filed: Jul. 13, 2007

(65) Prior Publication Data

US 2008/0026415 A1  Jan. 31, 2008

Related U.S. Application Data

(60) Provisional application No. 60/830,894, filed on Jul. 13, 2006.

(51) Int. Cl.
  *C12Q 1/48* (2006.01)
(52) U.S. Cl. ....................................... 435/15
(58) Field of Classification Search ........................ None
  See application file for complete search history.

(56) References Cited

U.S. PATENT DOCUMENTS

| | | | |
|---|---|---|---|
| 4,998,284 A | 3/1991 | Bacus et al. | |
| 5,386,819 A | 2/1995 | Kaneko et al. | |
| 5,784,162 A | 7/1998 | Cabib et al. | |
| 5,989,835 A | 11/1999 | Dunlay et al. | |
| 5,998,151 A | 12/1999 | Johnston et al. | |
| 6,026,174 A | 2/2000 | Palcic et al. | |
| 6,151,405 A | 11/2000 | Douglass et al. | |
| 6,165,734 A | 12/2000 | Garini et al. | |
| 6,215,892 B1 | 4/2001 | Douglass et al. | |
| 6,229,649 B1 | 5/2001 | Woods et al. | |
| 6,251,601 B1 | 6/2001 | Bao et al. | |
| 6,337,472 B1 | 1/2002 | Garner et al. | |
| 6,466,690 B2 | 10/2002 | Bacus et al. | |
| 6,727,071 B1 | 4/2004 | Dunlay et al. | |
| 7,050,087 B2 | 5/2006 | Harari et al. | |
| 7,219,016 B2 | 5/2007 | Rimm et al. | |
| 2003/0036855 A1 | 2/2003 | Harris et al. | |
| 2005/0227303 A1 | 10/2005 | Guo et al. | |
| 2006/0127928 A1 | 6/2006 | Bacus et al. | |
| 2006/0147959 A1 | 7/2006 | Bell et al. | |
| 2006/0275844 A1 | 12/2006 | Linke et al. | |
| 2008/0013816 A1 | 1/2008 | Rimm et al. | |
| 2008/0026420 A1 | 1/2008 | Rimm et al. | |
| 2008/0046190 A1 | 2/2008 | Rimm et al. | |
| 2008/0056553 A1 | 3/2008 | Rimm et al. | |
| 2009/0155767 A1 | 6/2009 | Rimm et al. | |

FOREIGN PATENT DOCUMENTS

| WO | WO 90/10276 | 9/1990 |
|---|---|---|
| WO | WO 97/04418 | 2/1997 |
| WO | WO 97/22848 | 6/1997 |
| WO | WO 99/47963 | 9/1999 |
| WO | WO 00/24940 | 5/2000 |
| WO | WO 00/31534 | 6/2000 |
| WO | WO 00/62247 | 10/2000 |
| WO | WO 01/20044 | 3/2001 |
| WO | WO 01/22086 | 3/2001 |
| WO | WO 02/086498 | 10/2002 |
| WO | WO 2008/008500 | 1/2008 |
| WO | WO 2009/005715 | 1/2009 |
| WO | WO 2009/005816 | 1/2009 |

OTHER PUBLICATIONS

Camp RL. et al. "Automated subcellular localization and quantification of protein expression in tissue microarrays", Nature Medicine, Nov. 2002, vol. 8, No. 11, pp. 1323-1327, entire document.*

Wong Nacs et al. "Nuclear thmidylate synthase expression, P53 expression and 5FU response in colorectal carcinoma", Br. J. Cancer, 2001, vol. 85, No. 12, pp. 1937-1943, entire document.*

Fernandez-Contreras et al. "Thymidylate synthase expression pattern is a prognostic factor in patients of colorectal cancer treated with 5-fluorouracil", Int. J. Oncol., Oct. 2004, vol. 25, No. 4, pp. 877-885, Abstract only.*

Santi DV. "The mechanism and structure of thymidylate synthetase," *Nucleic Acids Symp Ser* 1986(17):125-6.

Berger SH, Berger FG. "Thymidylate synthase as a determinant of 5-fluoro-2'-deoxyuridine response in human colonic tumor cell lines," *Mol Pharmacol* 1988;34(4):474-9.

Johnston PG, Drake JC, Trepel J, Allegra CJ. "Immunological quantitation of thymidylate synthase using the monoclonal antibody TS 106 in 5-fluorouracil-sensitive and -resistant human cancer cell lines," *Cancer Res* 1992;52(16):4306-12.

Johnston PG, Lenz HJ, Leichman CG, Danenberg KD, Allegra CJ, Danenberg PV, et al. "Thymidylate synthase gene and protein expression correlate and are associated with response to 5-fluorouracil in human colorectal and gastric tumors," *Cancer Res* 1995;55(7):1407-12.

Leichman CG, Lenz HJ, Leichman L, Danenberg K, Baranda J, Groshen S, et al. "Quantitation of intratumoral thymidylate synthase expression predicts for disseminated colorectal cancer response and resistance to protracted-infusion fluorouracil and weekly leucovorin," *J Clin Oncol* 1997;15(10):3223-9.

Edler D, Glimelius B, Hallstrom M, Jakobsen A, Johnston PG, Magnusson I, et al. "Thymidylate synthase expression in colorectal cancer: a prognostic and predictive marker of benefit from adjuvant fluorouracil-based chemotherapy," *J Clin Oncol* 2002;20(7):1721-8.

(Continued)

*Primary Examiner*—Sandra Saucier
*Assistant Examiner*—Satyendra K Singh
(74) *Attorney, Agent, or Firm*—Cooper & Dunham LLP; John P. White

(57) ABSTRACT

This invention provides a method of making a prognosis for a patient afflicted with a type of cancer such as colon cancer, based upon quantification of biomarkers such as thymidylate synthase in subcellular compartments.

16 Claims, 13 Drawing Sheets

OTHER PUBLICATIONS

Edler D, Kressner U, Ragnhammar P, Johnston PG, Magnusson I, Glimelius B, et al. "Immunohistochemically detected thymidylate synthase in colorectal cancer: an independent prognostic factor of survival," *Clin Cancer Res* 2000;6(2):488-92.

Aschele C, Lonardi S, Monfardini S. "Thymidylate Synthase expression as a predictor of clinical response to fluoropyrimidine-based chemotherapy in advanced colorectal cancer," *Cancer Treat Rev* 2002;28(1):27-47.

Popat S, Matakidou A, Houlston RS. "Thymidylate synthase expression and prognosis in colorectal cancer: a systematic review and meta-analysis," *J Clin Oncol* 2004;22(3):529-36.

Leichman CG. "Thymidylate synthase as a predictor of response," *Oncology* (Williston Park) 1998;12(8 Suppl 6):43-7.

Leichman L, Lenz HJ, Leichman CG, Groshen S, Danenberg K, Baranda J, et al. "Quantitation of intratumoral thymidylate synthase expression predicts for resistance to protracted infusion of 5-fluorouracil and weekly leucovorin in disseminated colorectal cancers: preliminary report from an ongoing trial," *Eur J Cancer* 1995;31A(7-8):1306-10.

Liu J, Schmitz JC, Lin X, Tai N, Yan W, Farrell M, et al. "Thymidylate synthase as a translational regulator of cellular gene expression," *Biochim Biophys Acta* 2002;1587(2-3):174-82.

Camp RL, Chung GG, Rimm DL. "Automated subcellular localization and quantification of protein expression in tissue microarrays," *Nat.Med.* 2002;8(11):1323-1327.

McCabe A, Dolled-Filhart M, Camp RL, Rimm DL. "Automated quantitative analysis (AQUA) of in situ protein expression, antibody concentration, and prognosis," *J Natl Cancer Inst* 2005;97(24):1808-15.

Berger AJ, Kluger HM, Li N, Kielhorn E, Halaban R, Ronai Z, et al. "Subcellular localization of activating transcription factor 2 in melanoma specimens predicts patient survival," 25. *Cancer Res.* 2003;63(23):8103-8107.

Rimm DL, Camp RL, Charette LA, Costa J, Olsen DA, Reiss M. "Tissue microarray: a new technology for amplification of tissue resources," *Cancer J.* 2001;7(1):24-31.

Rimm DL, Camp RL, Charette LA, Olsen DA, Provost E. "Amplification of tissue by construction of tissue microarrays," *Exp Mol Pathol* 2001;70(3):255-64.

Giltnane JM, Rimm DL. "Technology insight: Identification of biomarkers with tissue microarray technology," *Nat Clin Pract Oncol* 2004;1(2):104-11.

Camp RL, Dolled-Filhart M, Rimm DL. "X-tile: a new bio-informatics tool for biomarker assessment and outcome-based cut-point optimization," 9. *Clin.Cancer Res.* 2004;10(21):7252-7259.

Raeside DE. "Monte Carlo principles and applications," *Phys Med Biol* 1976;21(2):181-97.

Camp RL, Charette LA, Rimm DL. "Validation of tissue microarray technology in breast carcinoma," 50. *Lab Invest* 2000;80(12):1943-1949.

Kucera R, Paulus H. "Localization of the deoxyribonucleotide biosynthetic enzymes ribonucleotide reductase and thymidylate synthase in mouse L cells," *Exp Cell Res* 1986;167(2):417-28.

Johnston PG, Liang CM, Henry S, Chabner BA, Allegra CJ. "Production and characterization of monoclonal antibodies that localize human thymidylate synthase in the cytoplasm of human cells and tissue," *Cancer Res* 1991;51(24):6668-76.

Bissoon-Haqqani S, Moyana T, Jonker D, Maroun JA, Birnboim HC, "Nuclear expression of thymidylate synthase in colorectal cancer cell lines and clinical samples," *J Histochem Cytochem* 2006;54(1):19-29.

Wong NA, Brett L, Stewart M, Leitch A, Longley DB, Dunlop MG, et al. "Nuclear thymidylate synthase expression, p53 expression and 5FU response in colorectal carcinoma," *Br J Cancer* 2001;85(12):1937-43.

International Preliminary Report on Patentability issued by the International Bureau in connection with International Application No. PCT/US2007/016014.

Written Opinion of the International Searching Authority issued by the International Searching Authority (ISA/US) in connection with International Application No. PCT/US2007/016014.

International Search Report issued by the International Bureau in connection with International Application No. PCT/US2007/016014.

Cascinue S. et al., "Thymidylate synthase protein expression in advanced colon cancer: correlation with the site of metastasis and the clinical response to Leucovorin-modulated bolus 5-fluorouracil," *Clinical Cancer Research*, Aug. 1999, vol. 5, pp. 1996-1999.

Elder D. et al., "Immunohistochemically detected thymidylate synthase in colorectal cancer: an independent prognostic factor of survival," *Clinical Cancer Research*, Feb. 2000, vol. 6, pp. 488-492.

Elder D. et al., "Thymidylate synthase expression in colorectal cancer: a prognostic and predictive marker of benefit from adjuvant fluorouracil-based chemotherapy," *Journal of Clinical Oncology*, Apr. 2002, vol. 20, No. 7, pp. 1721-1728.

Santini D. et al. "Thymidylate synthase expression in normal colonic mucosa: a predictive marker of toxicity in colorectal cancer patients receiving 5-fluorouracil-based adjuvant chemotherapy," *Oncology*, 2004, vol. 67, pp. 135-142.

Arnold et al., "Molecular Determinants for Subcellular Localization of PSD-95 with an Interacting K+ Channel," *Neuron*, May 1999, 24:149-157.

Chen et al., "Ratio-Based Decisions and the Quantitative Analysis of cDNA Microarray Images," *J. Biomed. Optics*, Oct. 1997, 2(4):364-374.

Forus et al., "Sensitive Fluorescent in situ Hybridisation Method for the Characterisation of Breast Cancer Cells in Bone Marrow Aspirates," *The Journal of Clinical Pathology*, 1999, 52:68-74.

Klein et al., "The Neuroimmune Interface in Prion Diseases," *News Physiol. Sci.*, Oct. 2000, 15:250-255.

Rigaut et al., "Three-Dimensional DNA Image Cytometry by Confocal Scanning Laser Microscopy in Thick Tissue Blocks," *Cytometry*, 1991, 12:511-524.

Staines et al., "Three-Color Immunofluorescence Histochemistry Allowing Triple Labeling Within a Single Section," *The Journal of Histochemistry and Cytochemistry*, 1988, 36(6):145-151.

Wood et al., "B-Spectrin is Colocalized with Both Voltage-gated Sodium Channels and AnkyrinG at the Adult Rat Neuromuscular Junction," *The Journal of Cell Biology*, 1998, 140(3):675-684.

Zhou et al., "A Multiple Wavelength Algorithm in Color Image Analysis and Its Applications in Stain Decomposition in Microscopy Images," *Med. Phys.*, 1996, 23(12):1977-1986.

International Search Report issued by the International Searching Authority in connection with International Application No. PCT/US2002/012804.

International Preliminary Examination Report issued by the International Bureau in connection with International Application No. PCT/US2002/012804.

Pending claims for U.S. Appl. No. 12/215,458, filed Jun. 27, 2008.
Pending claims for U.S. Appl. No. 11/789,361, filed Apr. 23, 2007.
Pending claims for U.S. Appl. No. 11/820,786, filed Jun. 20, 2007.
Pending claims for U.S. Appl. No. 11/894,297, filed Aug. 20, 2007.
Pending claims for U.S. Appl. No. 11/894,680, filed Aug. 20, 2007.
Dec. 18, 2003 Office Action issued in connection with U.S. Appl. No. 10/062,308, filed Feb. 1, 2002, now U.S. Patent No. 7,219,016.
Jun. 16, 2004 Office Action issued in connection with U.S. Appl. No. 10/062,308, filed Feb. 1, 2002, now U.S. Patent No. 7,219,016.
Apr. 7, 2005 Office Action issued in connection with U.S. Appl. No. 10/062,308, filed Feb. 1, 2002, now U.S. Patent No. 7,219,016.
Oct. 19, 2005 Office Action issued in connection with U.S. Appl. No. 10/062,308, filed Feb. 1, 2002, now U.S. Patent No. 7,219,016.
Apr. 27, 2006 Office Action issued in connection with U.S. Appl. No. 10/062,308, filed Feb. 1, 2002, now U.S. Patent No. 7,219,016.
Nov. 24, 2006 Office Action issued in connection with U.S. Appl. No. 10/062,308, filed Feb. 1, 2002, now U.S. Patent No. 7,219,016.
Supplemental European Search report issued by European Patent Office in connection with International Application No. PCT/US2002/012084.

Agard D A, "Optical Sectioning Microscopy: Cellular Architecture in Three Dimensions," *Annual Review of Biophysics and Bioengineering, Annual Reviews Inc.*, vol. 13, Jan. 1, 1984, pp. 191-219.

Examiner's Report issued Nov. 15, 2006 by the Australian Patent Office in connection with Australian Patent Application No. 2002311827, now Australian Patent No. 2002311827 (national stage of PCT International Application No. PCT/US02/12084).

Office Action issued Oct. 20, 2009 by the Canadian Patent Office in connection with Canadian Patent Application No. 2442604 (national stage of PCT International Application No. PCT/US02/12084).

English translation of Official Action issued Jul. 4, 2007 by the Japanese Patent Office in connection with Japanese Patent Application No. 2002-583976 (national stage of PCT International Application No. PCT/US02/12084).

English translation of Official Action issued May 19, 2008 by the Japanese Patent Office in connection with Japanese Patent Application No. 2002-583976 (national stage of PCT International Application No. PCT/US02/12084).

English translation of Official Action issued Apr. 10, 2009 by the Japanese Patent Office in connection with Japanese Patent Application No. 2002-583976 (national stage of PCT International Application No. PCT/US02/12084).

International Search Report issued by the International Bureau in connection with International Application No. PCT/US2008/08229.

Written Opinion of the International Searching Authority issued by the International Searching Authority (ISA/US) in connection with International Application No. PCT/US2008/08229.

Matsumoto et al. "Markers of cell proliferation and expression of melanosomal antigen in lymphangioleimyomatosis," *Am. J. Respir. Cell. Mol. Biol.* Sep. 1999, vol. 21, No. 3 pp. 327-336.

Vollmer et al. "Use of Bayes Rule and MIB-1 Proliferation Index to Discriminate Spitz Nevus From Malignant Melanoma," *Am. J. Olin. Pathol.* 2004, vol. 122, pp. 499-505.

Sundram et al. "Expression of the B-Cell Proliferation Marker MUM1 by Melanocytic Lesions and Comparison with S100, gp100 (HMB45), and MelanA," *Mod. Pathol.* 2003, vol. 16, No. 8 pp. 802-810.

International Search Report issued by the International Bureau in connection with International Application No. PCT/US2008/08007.

Written Opinion of the International Searching Authority issued by the International Searching Authority (ISA/US) in connection with International Application No. PCT/US2008/08007.

\* cited by examiner

A.

Inset:

Inset:

A.

Inset:

B.

Inset:

Inset:

B.

Inset:

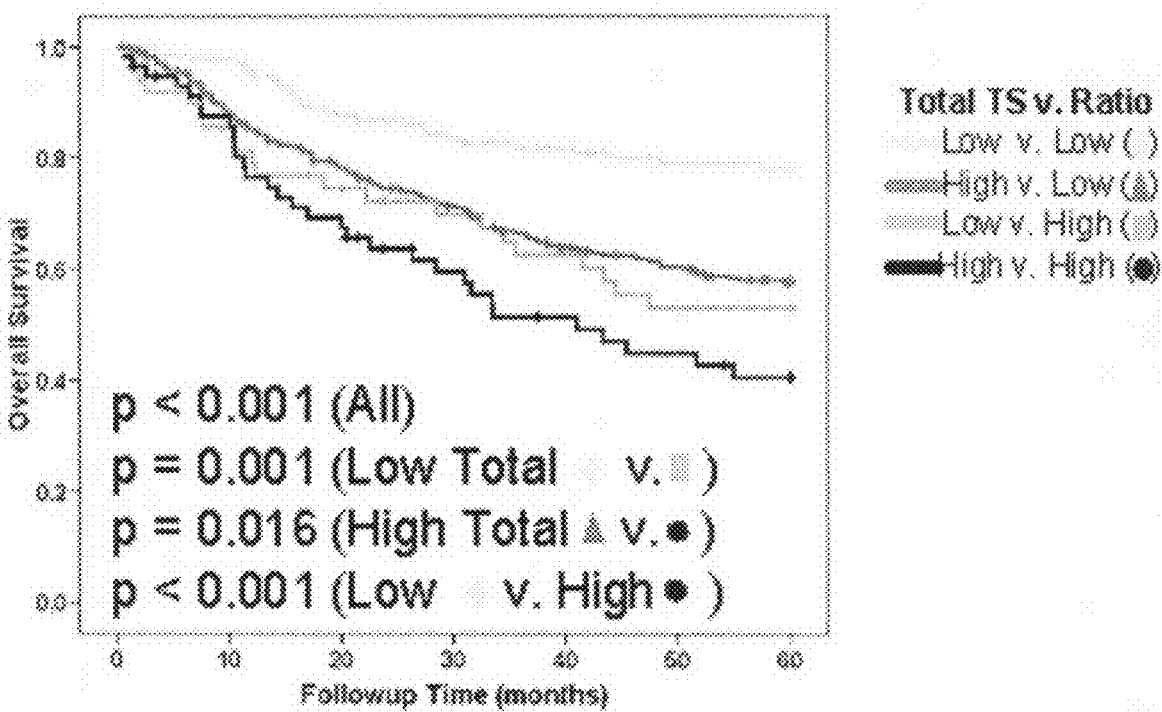

METHODS FOR MAKING CANCER PROGNOSES BASED ON SUBCELLULAR LOCALIZATION OF BIOMARKERS

This application claims benefit of U.S. Provisional Application No. 60/830,894, filed Jul. 13, 2006; the contents of which in its entirety is hereby incorporated by reference into this application.

Throughout this application, various publications are referenced in parentheses by author name and date, or by a patent or patent publication number. Full citations for these publications may be found at the end of the specification immediately preceding the claims. The disclosures of each of these publications in its entirety are hereby incorporated by reference into this application in order to more fully describe the state of the art as known to those skilled therein as of the date of this application.

BACKGROUND OF THE INVENTION

Colorectal cancer is among the leading causes of cancer-related morbidity and mortality in industrialized nations. Patients diagnosed at an early stage, prior to lymph-node spread, are potentially cured with surgery. While many patients are diagnosed at an early stage, most patients frequently undergo peri-operative radiation and/or chemotherapy to attempt to control the metastatic spread of disease. Ultimately, many patients thought to have undergone curative resections eventually develop recurrent disease. Factors that enhance survival include accurate and early diagnosis and prediction of survival and response to therapy, as colon and rectal cancers are often silent and slowly progressive.

Thus, there is a need for identifying colon cancer early in the course of the disease process, and a particular need for identifying cancers that are chemoresistant. More specifically, since it is understood in the art that the behavior of cancer cells, both regarding their tumorigenicity and their resistance to chemotherapeutic drugs is mediated by the expression of a not completely defined set of particular genes, there is a need to identify genes and collections or sets of genes that serve as effective molecular markers for chemoresistance in colon cancer, as well as such genes or gene sets that provide clinically effective therapeutic targets for colon cancer.

The majority of oncologic therapeutics specifically target proteins in cancer cells, therefore measurement of protein expression is important in determining the potential efficacy of such therapeutics. Assays detecting thymidylate synthase (TS) in tissue samples are known and studies investigating the relationship between TS expression and survival in colorectal cancer patients have been done. Most have shown poorer overall survival and progression free survival with high TS expression but results have varied widely and the precise prognostic value of TS is not yet known (Popat et al Journal of Clinical Oncology 22(3) Feb. 1, 2004, Thymidylate Synthase Expression and Prognosis in Colorectal Cancer: A Systematic Review and Meta-Analysis. New methods for consistent measurement of TS is tissue sections are needed.

Thymidylate synthase (TS) catalyzes the reductive methylation of deoxyuridylate for production of dTTP, which is critical for DNA synthesis. The regulation of its expression has been shown to be critical in modulation of response to 5-FU, a longstanding chemotherapeutic agent for colon cancer. High expression levels have been shown to be a marker for decreased survival and response to therapy. Recently, it has been demonstrated that TS may have other cellular functions, including post-transcriptional regulation.

SUMMARY OF THE INVENTION

This invention provides a method of making a prognosis for a patient afflicted with a type of cancer which comprises determining a quantity of a particular biomarker present within a first subcellular compartment and a quantity of such particular biomarker present within a second subcellular compartment in cells of interest present in a tissue sample from the patient, obtaining a ratio of the quantity of the biomarker present within the first subcellular compartment relative to the quantity of the particular biomarker present within the second subcellular compartment, and correlating the ratio so obtained with a series of predetermined ratios associated with a series of prognoses so as to thereby make a prognosis for the patient.

The invention also provides a method for determining a stage of advancement for a type of cancer in a patient which comprises (a) determining a quantity of a particular biomarker present within a first subcellular compartment and a quantity of a particular biomarker present within a second subcellular compartment in cells of interest present in a tissue sample from the patient; (b) obtaining a ratio of the quantity of the biomarker present within the first subcellular compartment relative to the quantity of the biomarker present within the second subcellular compartment; (c) comparing the ratio so obtained to a plurality of standard reference ratios associated with a series of stages of the type of cancer, and (d) determining the stage of advancement of the type of cancer based on the standard reference ratio closer to the ratio so obtained.

This invention also provides a method for selecting an appropriate therapy for a patient afflicted with a type of cancer which comprises (a) determining a quantity of a particular biomarker present within a first subcellular compartment and a quantity of such biomarker present within a second subcellular compartment in cells of interest present in a tissue sample from the patient; (b) obtaining a ratio of the quantity of the biomarker present within the first subcellular compartment relative to the quantity of the particular biomarker present within the second subcellular compartment; (c) comparing the ratio so obtained to a plurality of standard reference ratios associated with responsiveness and nonresponsiveness of cells of such type of cancer to treatment with each of a number of possible therapies, wherein the appropriate therapy for the patient is selected based on the reference ratio numerically closest to the ratio obtained.

This invention also provides a method for determining the likelihood a particular therapy will be successful for a patient afflicted with a type of cancer comprising (a) determining a quantity of a particular biomarker present within a first subcellular compartment and a quantity of such biomarker present within a second subcellular compartment in cells of interest present in a tissue sample from a patient; (b) obtaining a ratio of the quantity of the biomarker present within the first subcellular compartment relative to the quantity of the particular biomarker present within the second subcellular compartment; and (c) comparing the ratio so obtained to a plurality of standard reference ratios associated with responsiveness and nonresponsiveness of such cells of such type of cancer to treatment with the particular therapy, wherein the likelihood of success of the particular therapy is determined based on the reference ratio numerically closest to the ratio obtained.

This invention also provides a kit comprising (a) a first stain specific for thymidylate synthase; (b) a second stain specific for a first subcellular compartment of a cell; (c) a third stain specific for a second subcellular compartment of a cell; and (d) instructions for using the kit.

Linear regression analysis between AQUA® scores of redundant tissue cores for 152 of 663 cases of the training set is shown graphically with indicated R- and Spearman's Rho values for A.) Nuclear, B.) Cytoplasmic, and C.) Expression ratio. D.) Linear regression analysis between nuclear AQUA® scores and expression ratios for the same redundant tissue cores.

Figure 3:
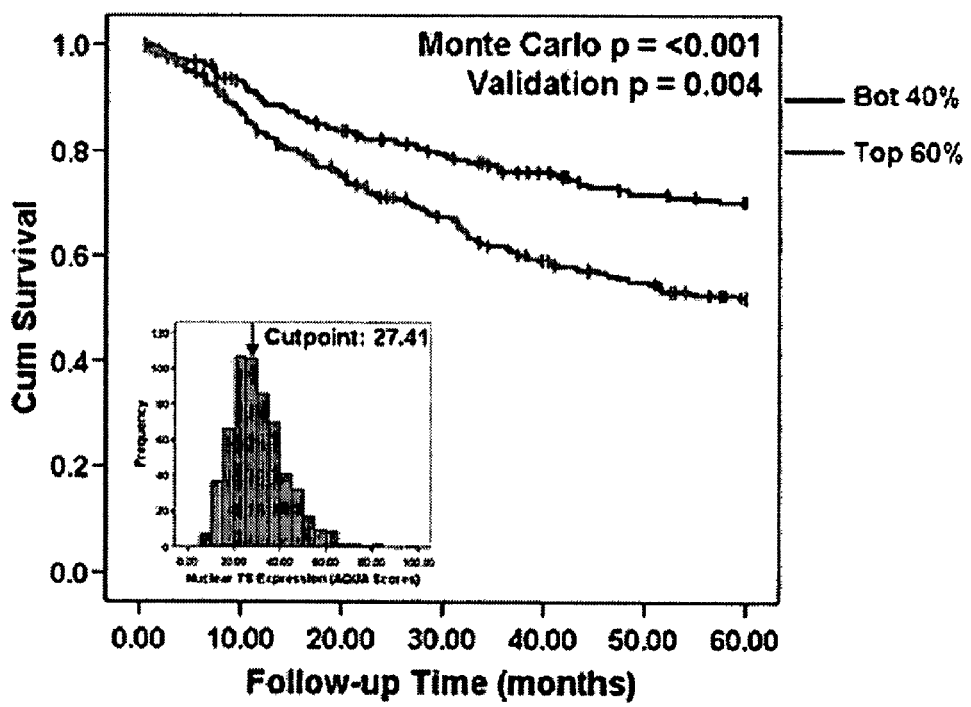
Figure 3:
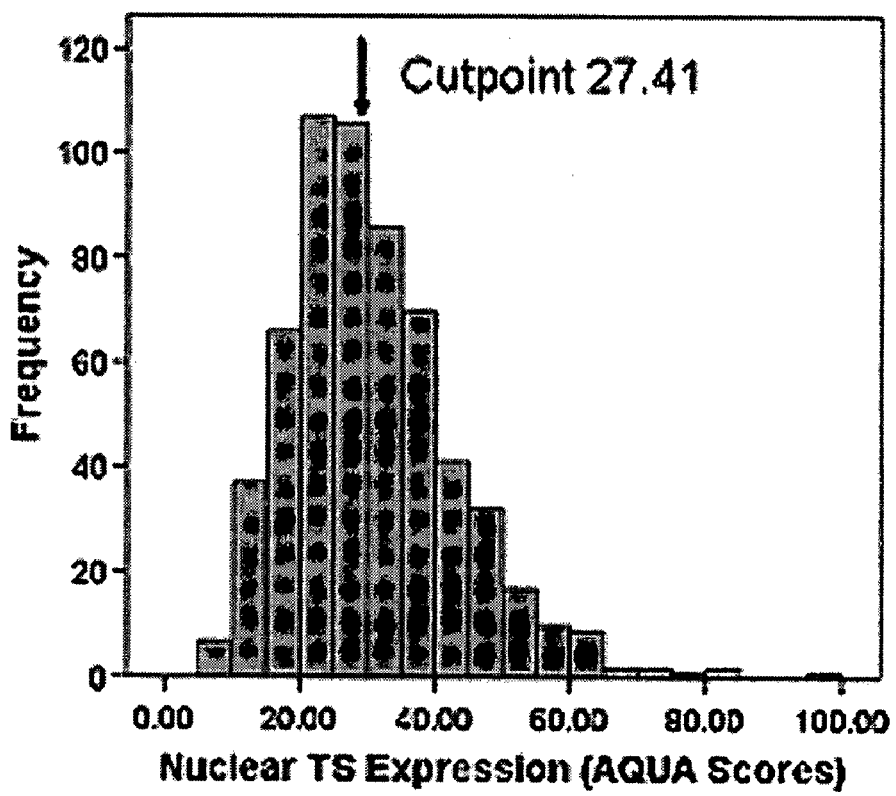
Figure 3:
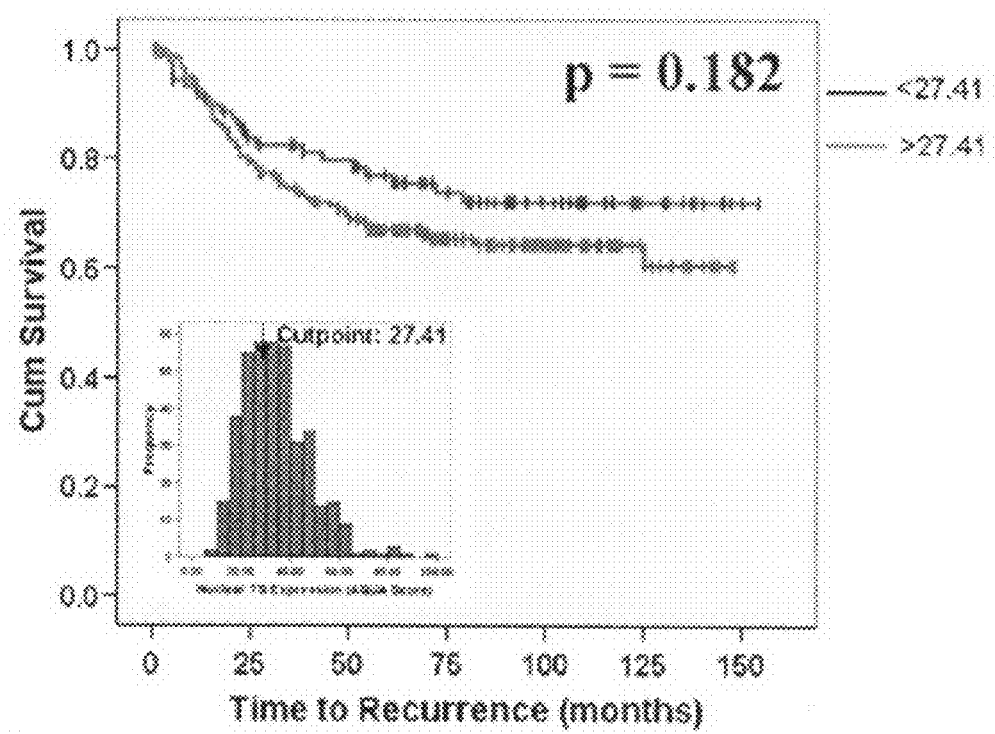
Figure 3:
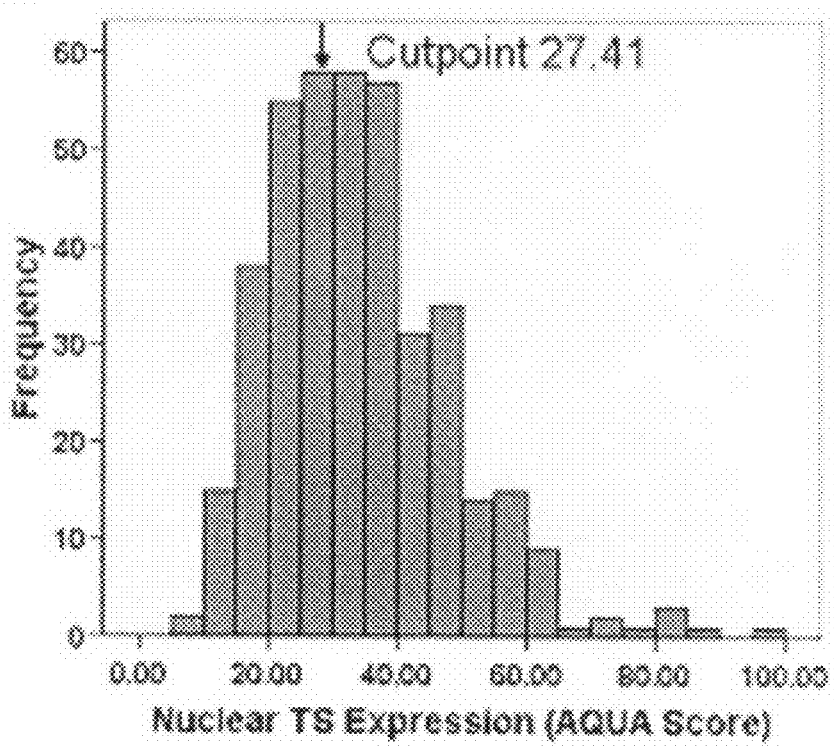

FIG. 3 is a Kaplan-Meir survival analysis of nuclear AQUA® scores.

Kaplan-Meier survival analysis on the training set (A) using optimal cutpoint selection (X-Tile™) showed a decrease in overall disease-specific patient survival from 72 to 56% for the top 60% of TS nuclear expressing tumors. Crosses indicate censored cases. Both Monte Carlo (robust statistic for optimal cutpoint selection) and training/validation (1:2 patient population ratio) p-values are highly significant, <0.001 and 0.004 respectively. Inset: Distribution analysis of nuclear TS AQUA® scores showing position of optimal cutpoint (27.41) within the distribution. This cutpoint was subsequently applied to a validation set using time to recurrence as the censor variable (B). As shown the cutpoint is not significant at p=0.182 given similar distribution of nuclear AQUA® scores (inset).

Figure 4:
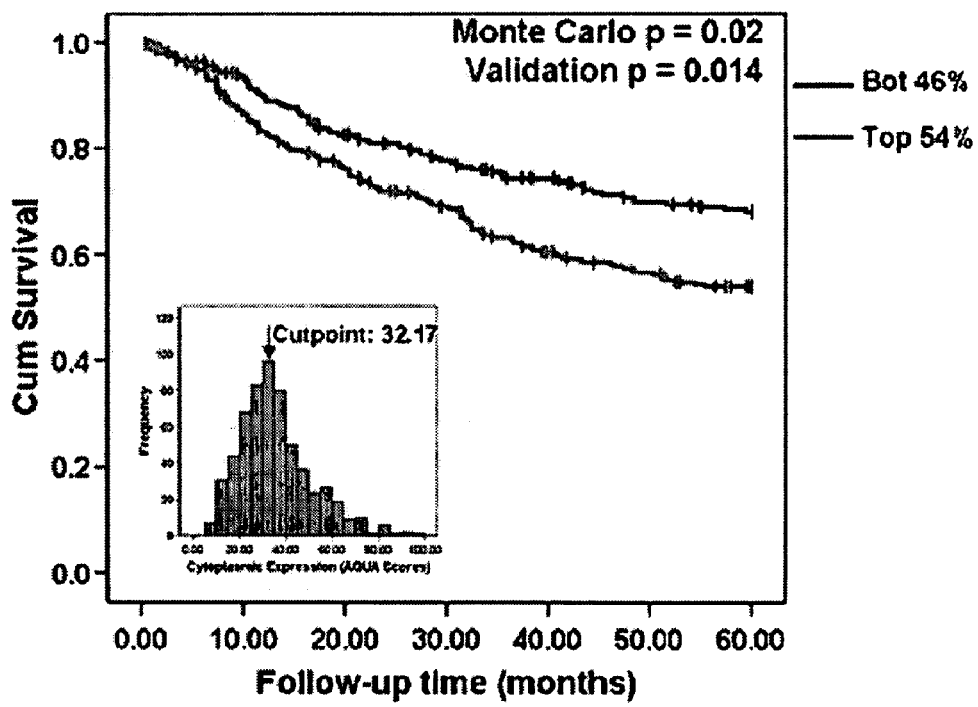
Figure 4:
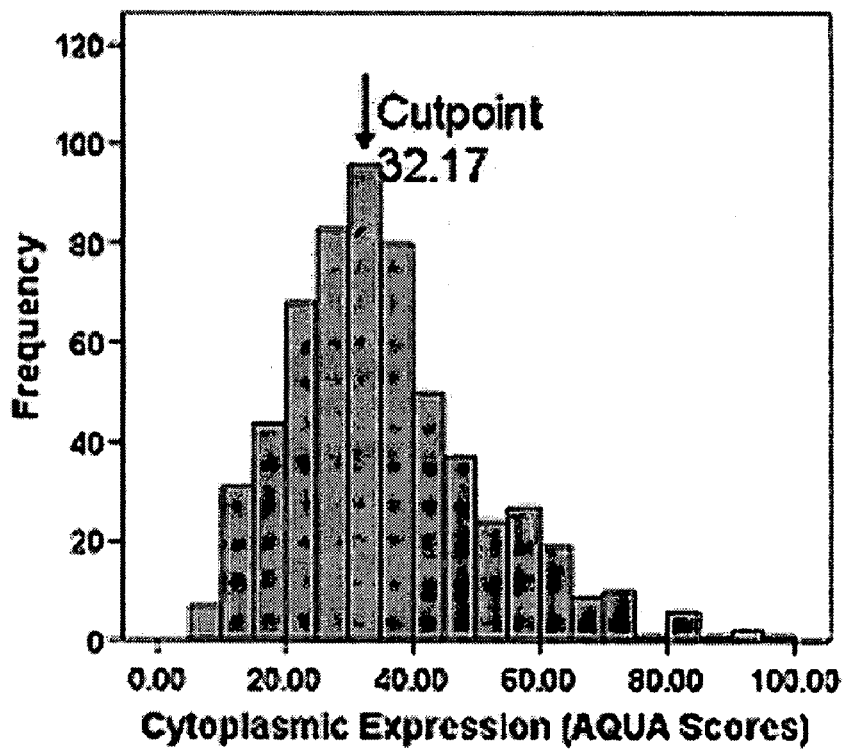
Figure 4:
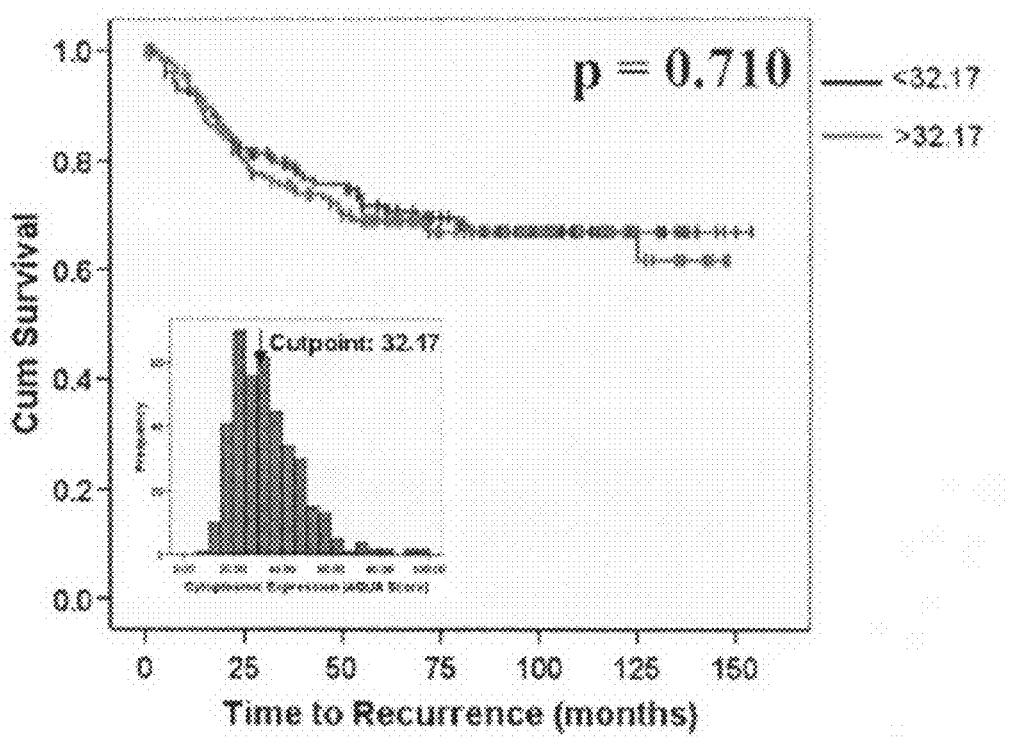
Figure 4:
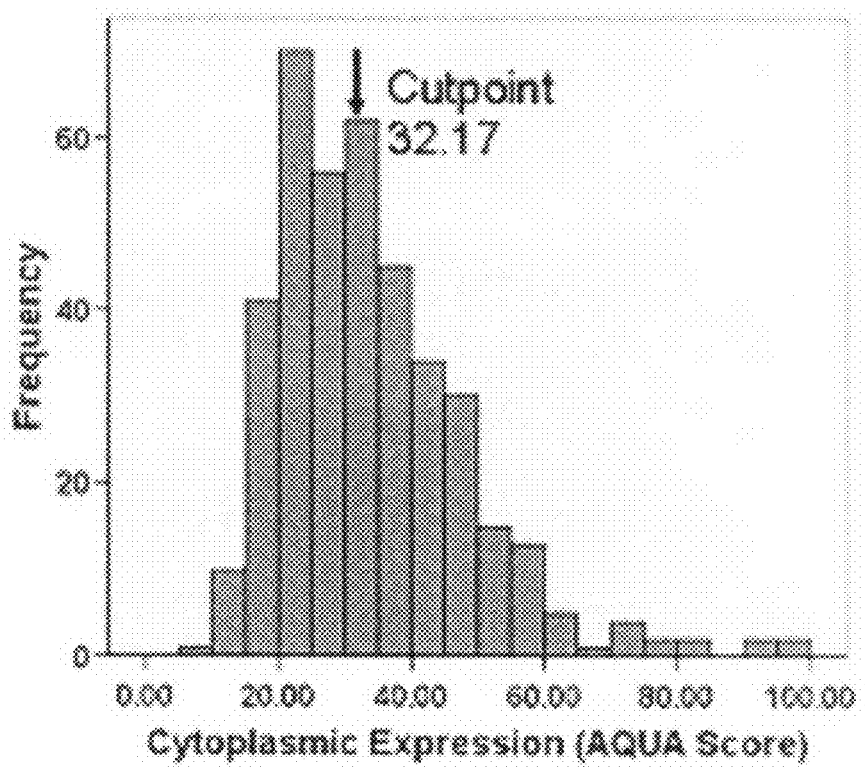

FIG. 4 is a Kaplan-Meier survival analysis of cytoplasmic AQUA® scores.

Kaplan-Meier survival analysis on the training set (A) using optimal cutpoint selection (X-tile™) showed a decrease in overall disease-specific patient survival from 70 to 58% for the top 54% of TS cytoplasmic expressing tumors. Crosses indicate censored cases. Both Monte Carlo (robust statistic for optimal cutpoint selection) and training/validation (1:2 patient population ratio) p-values are significant, 0.02 and 0.014 respectively. Inset: Distribution analysis of cytoplasmic TS AQUA® scores showing position of optimal cutpoint (32.17) within the distribution. This cutpoint was subsequently applied to a validation set using time to recurrence as the censor variable (B). As shown the cutpoint is not significant at p=0.710 given similar distribution of cytoplasmic AQUA® scores (inset).

Figure 5:
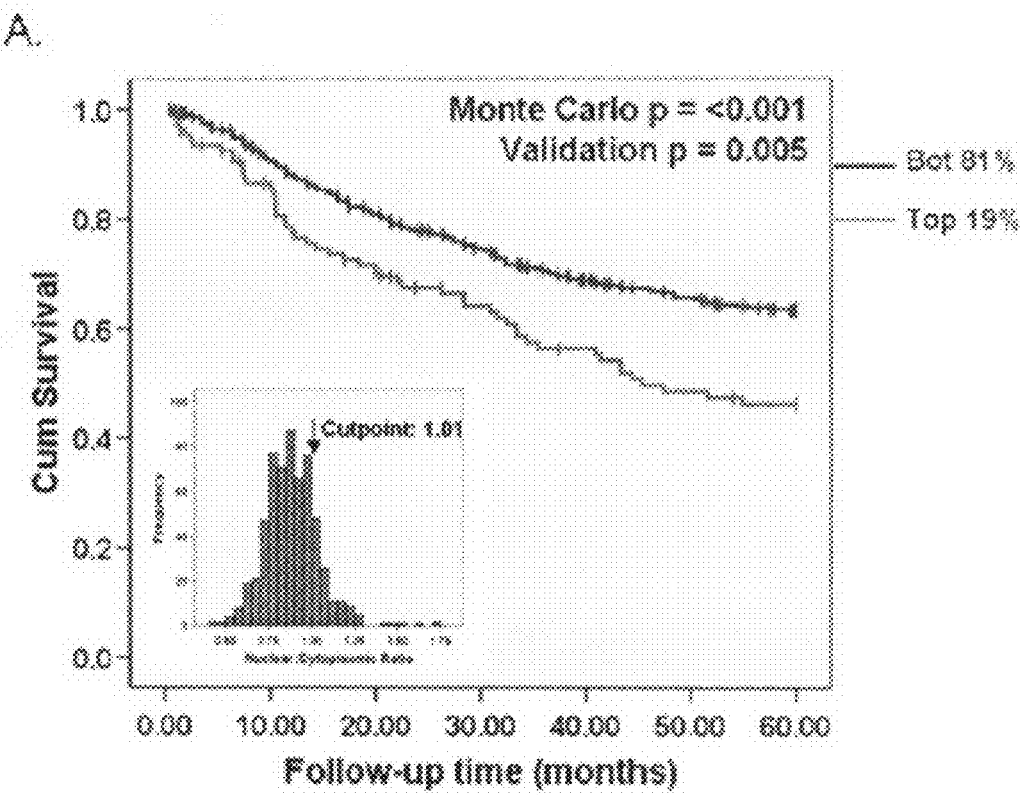
Figure 5:
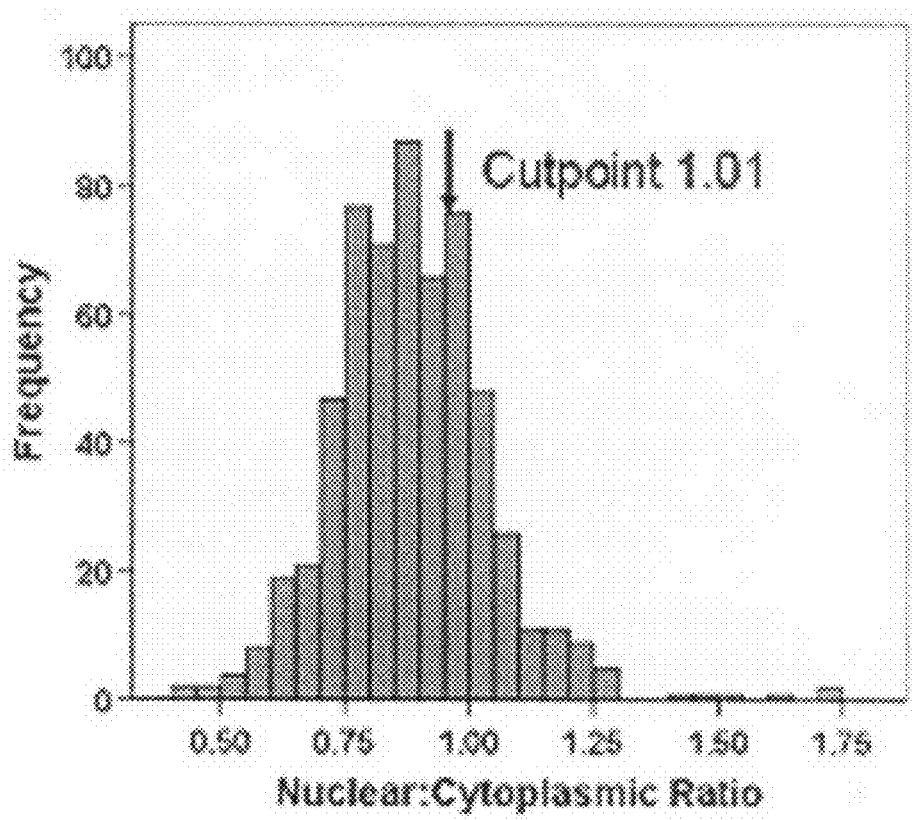
Figure 5:
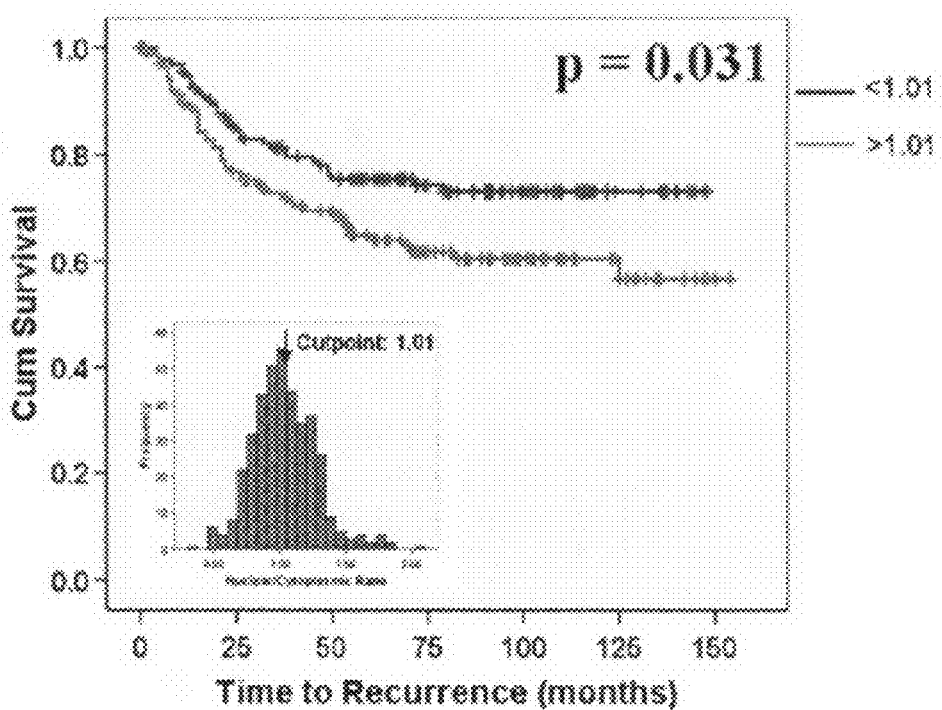
Figure 5:
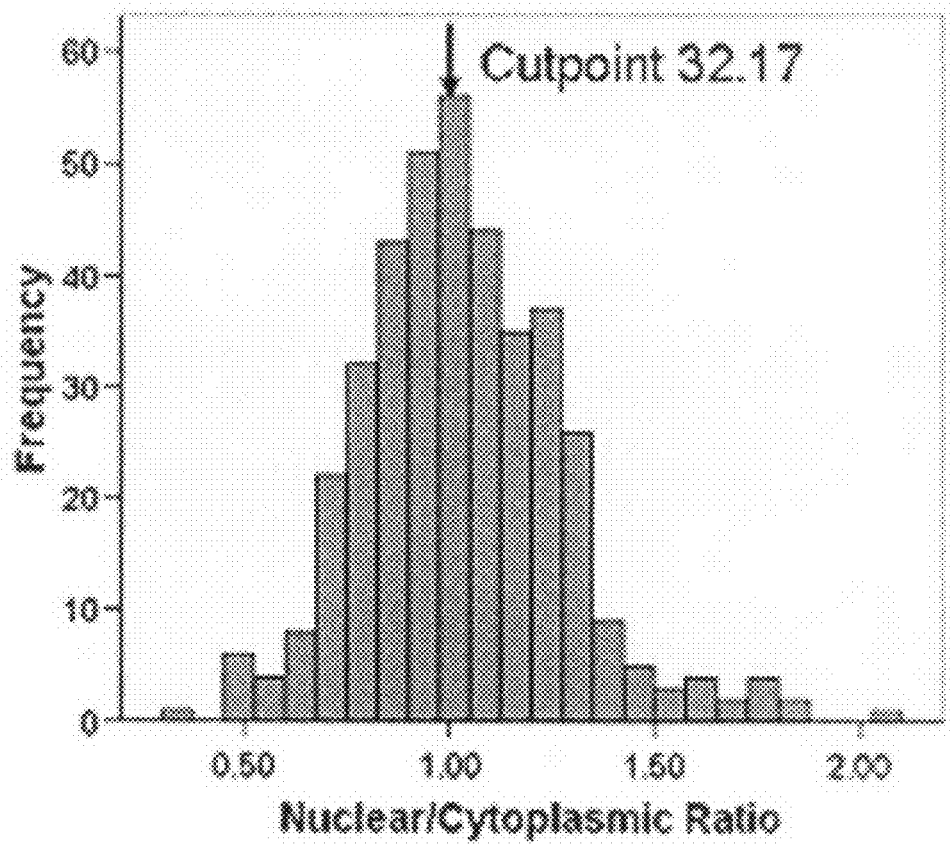

FIG. 5 is a Kaplan-Meier survival analysis of the expression ratio of nuclear-to-cytoplasmic AQUA® scores.

Kaplan-Meier survival analysis on the training set (A) using optimal cutpoint selection (X-Tile™) showed a decrease in overall patient survival from 66 to 51% for the top 19% of nuclear/cytoplasmic ratio tumors. Crosses indicate censored cases. Both Monte Carlo (robust statistic for optimal cutpoint selection) and training/validation (1:2 patient population ratio) p-values are highly significant, <0.001 and 0.005 respectively. Inset: Distribution analysis of TS ratio scores showing position of optimal cutpoint (1.01) within the distribution. This cutpoint was subsequently applied to a validation set using time to recurrence as the censor variable (right). As shown the cutpoint is significant at p=0.031.

Figure 6:
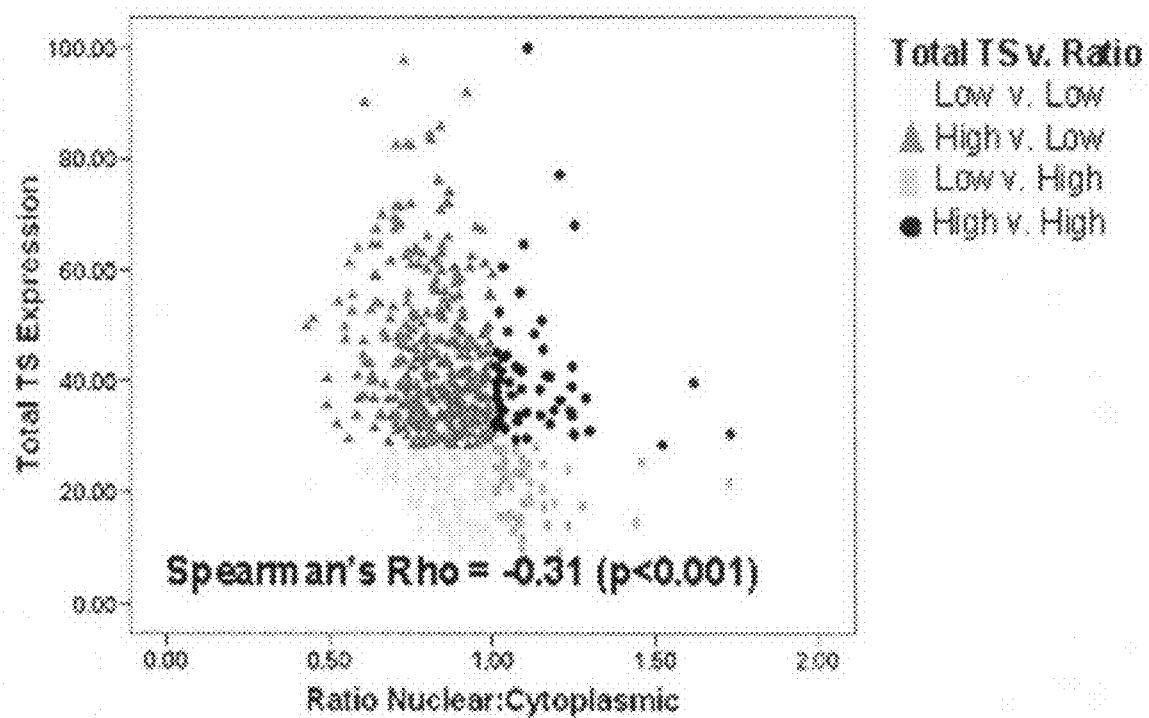

FIG. 6 shows TS Multiplexing on the Training Set

A) Total TS expression values (Y-axis) and nuclear:cytoplasmic ratios (X-axis) were regressed, with groupings, as defined by optimal X-Tile cutpoints, as indicated.

B.) Kaplan-Meier five-year disease specific survival analysis of indicated groups (A).

Figure 7:
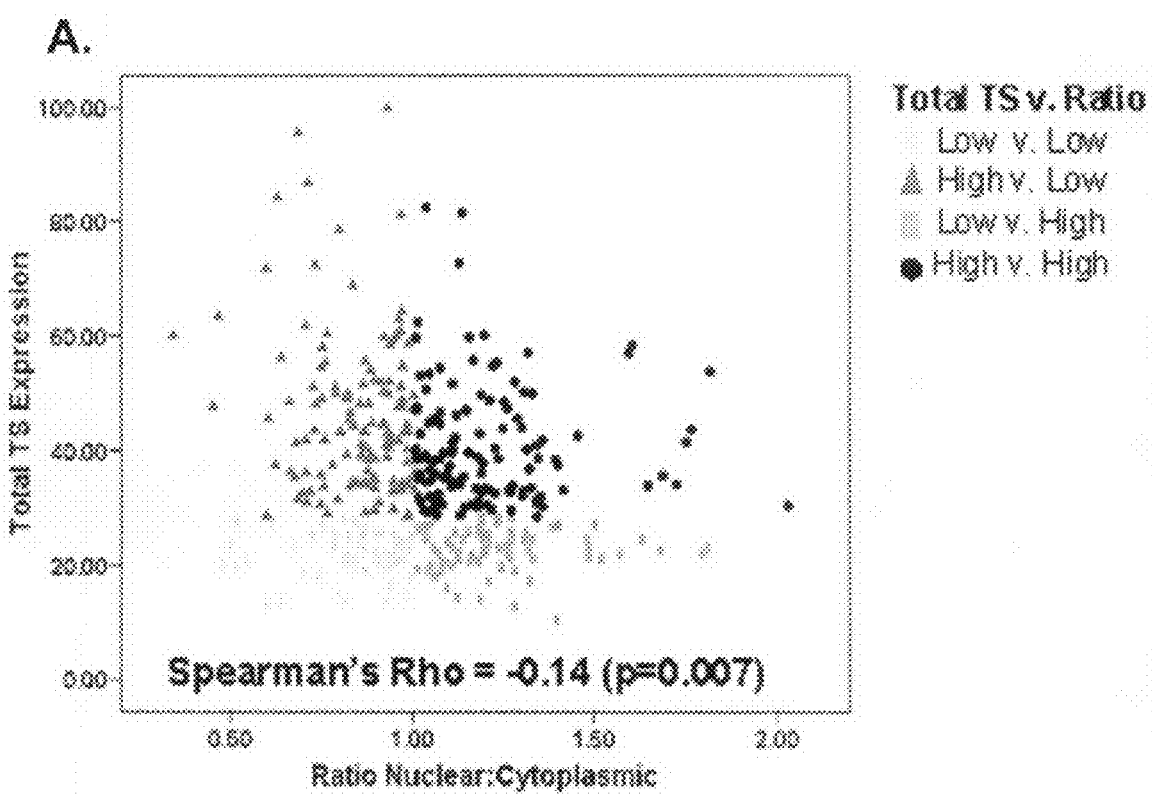
Figure 7:
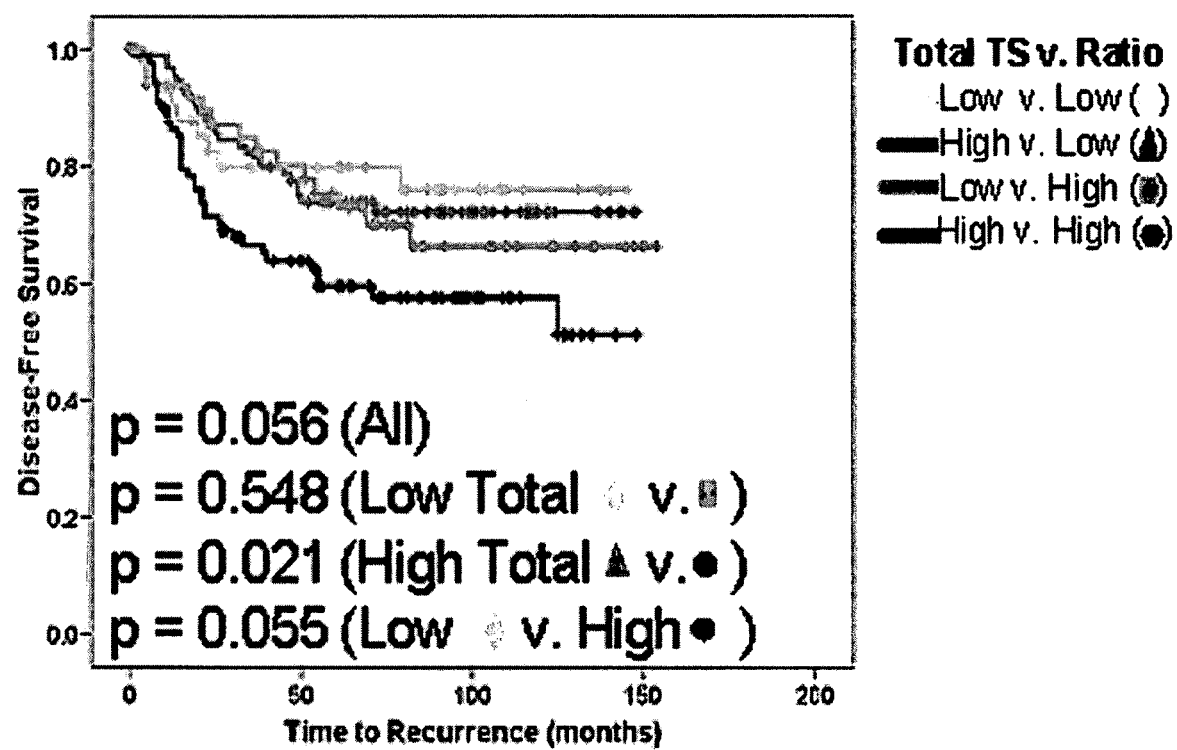

FIG. 7 shows TS Multiplexing on the Validation Set

A) Total TS expression (Y-axis) and nuclear:cytoplasmic ratios (X-axis) were regressed, with groupings, as defined by optimal X-Tile cutpoints from training set, as indicated.

B.) Kaplan-Meier recurrence-specific survival analysis of indicated groups from (A).

DETAILED DESCRIPTION OF THE INVENTION

For convenience, before further description of the present invention, certain terms employed in the specification, examples and appended claims are defined here.

The term "tissue sample" refers to a sample obtained from an organism.

A "patient", "subject" or "host" to be treated by the subject method may include either a human or non-human animal.

The term "prognosis" refers to a prediction of how a patient's disease will progress; and/or whether there is a chance for recovery; and/or how the patient will respond to treatment.

The "stage of advancement" refers to at the point in the natural evolution of the disease which the patient is at the time a method according to the invention is performed.

"Cells of interest" refers to cells obtained from a cancer patient.

A "reference ratio" refers to a ratio of the quantity of a particular biomarker within a first subcellular compartment relative to the quantity of a particular biomarker within a second subcellular compartment wherein the former is the numerator and the latter is the denominator.

Colon cancer refers to colon or colorectal cancer.

Thus, this invention provides a method of making a prognosis for a patient afflicted with a type of cancer which comprises determining a quantity of a particular biomarker present within a first subcellular compartment and a quantity of such particular biomarker present within a second subcellular compartment in cells of interest present in a tissue sample from the patient, obtaining a ratio of the quantity of the biomarker present within the first subcellular compartment relative to the quantity of the particular biomarker present within the second subcellular compartment, and correlating the ratio so obtained with a series of predetermined ratios associated with a series of prognoses so as to thereby make a prognosis for the patient.

In one embodiment, the particular biomarker is thymidylate synthase.

In certain embodiments, the type of cancer is colon cancer. In other embodiments, the type of cancer may be breast cancer, skin cancer, thyroid cancer, prostate cancer, kidney cancer, pancreatic cancer, lung cancer, bladder cancer, rectal cancer, or leukemia.

In one embodiment, the first subcellular compartment is a nuclear compartment and the second subcellular compartment is a cytoplasmic compartment. In another embodiment, the first and second subcellular compartments refer to any of a number of other subcellular compartments including but not limited to cell membrane, endoplasmic reticulum, golgi, lysosomes, and/or any compartment that can be labeled molecularly.

In one embodiment, the quantity of the particular biomarker present within the first and the quantity of the particular biomarker present within the second subcellular compartments is each determined using an automated pathology system.

In a more specific embodiment, the automated pathology system used to determine the quantities of the particular biomarker present within the first and the quantity of the particular biomarker present within the second subcellular compartments is the AQUA® system and employs the method described in U.S. Pat. No. 7,219,016 B2, issued May 15, 2007, the contents of which are hereby incorporated in its entirety by reference in this application.

In another embodiment, the quantity of the biomarker is determined by reverse transcription-polymerase chain reaction (RT-PCR), dot blot analysis, Northern blots, serial analysis of gene expression (SAGE) or in situ hybridization.

In certain embodiments, the method is performed in a multiplex format wherein the biomarker ratio is determined along with the expression of epidermal growth factor receptor, HER1, HER2, HER3, H3R4, defensin alpha6, Pms2, SZ-Catenin, CTNNB1, LRP5, GSK3SZ, Axin-1, CtBP1, CD137/CD137L, BCRP/ABCG2, CD80 (B7-1), CD86 (B7-2), ALCAM, CKB, hnRNP F, E-cadherin, beta-catenin and CD-44v6, Ep-CAM, bcl-2, p53, Ki-67, cyclin D1, carcinoembryonic antigen, neuropilin (NRP), PIK3Ca, c-myc p64, c-myc p67, CYP1B1, aryl hydrocarbon receptor (AhR), PRL-1, PRL-2, PRL-3, Tenascin C, TUCAN, glucose-regulated protein 78, aberrant cytochrome c oxidase subunit I, or Galectin-3.

In one embodiment, predetermined ratios greater than one are associated with an unfavorable prognosis for the patient.

In another embodiment, predetermined ratios less than one are associated with a favorable prognosis for the patient.

In some embodiments, the ratio obtained is compared to a plurality of standard reference ratios each of which is associated with a predicted survival time, wherein the prognosis for the patient is correlated with the reference ratio numerically closest to the ratio obtained.

In other embodiments, the relationship is determined between (a) the ratio obtained and (b) the total of the quantity of the biomarker present within the first subcellular compartment and the quantity of the biomarker present within the second subcellular compartment and correlating the relationship so determined with the patient's prognosis.

The invention also provides a method for determining a stage of advancement for a type of cancer in a patient which comprises (a) determining a quantity of a particular biomarker present within a first subcellular compartment and a quantity of a particular biomarker present within a second subcellular compartment in cells of interest present in a tissue sample from the patient; (b) obtaining a ratio of the quantity of the biomarker present within the first subcellular compartment relative to the quantity of the biomarker present within the second subcellular compartment; (c) comparing the ratio so obtained to a plurality of standard reference ratios associated with a series of stages of the type of cancer, and (d) determining the stage of advancement of the type of cancer based on the standard reference ratio closer to the ratio so obtained.

In one embodiment, the particular biomarker is thymidylate synthase.

In another embodiment, the type of cancer is colon cancer. In other embodiments, the type of cancer may be breast cancer, skin cancer, thyroid cancer, prostate cancer, kidney cancer, pancreatic cancer, lung cancer, bladder cancer, rectal cancer, or leukemia.

In another embodiment, the first subcellular compartment is a nuclear compartment and the second subcellular compartment is a cytoplasmic compartment. In another embodiment, the first and second subcellular compartments refer to any of a number of other subcellular compartments including but not limited to cell membrane, endoplasmic reticulum, golgi, lysosomes, and/or any compartment that can be labeled molecularly.

In one embodiment, the quantity of the particular biomarker present within the first and the quantity of the particular biomarker present within the second subcellular compartments is each determined using an automated pathology system.

In one embodiment, the patient is undergoing cancer therapy and the stage of advancement for the type of cancer is determined at specific time intervals so as to thereby assess the effectiveness of the therapy.

This invention also provides a method for selecting an appropriate therapy for a patient afflicted with a type of cancer which comprises (a) determining a quantity of a particular biomarker present within a first subcellular compartment and a quantity of such biomarker present within a second subcellular compartment in cells of interest present in a tissue sample from the patient; (b) obtaining a ratio of the quantity of the biomarker present within the first subcellular compartment relative to the quantity of the particular biomarker present within the second subcellular compartment; (c) comparing the ratio so obtained to a plurality of standard reference ratios associated with responsiveness and nonresponsiveness of cells of such type of cancer to treatment with each of a number of possible therapies, wherein the appropriate therapy for the patient is selected based on the reference ratio numerically closest to the ratio obtained.

In one embodiment, the particular biomarker is thymidylate synthase.

In another embodiment, the type of cancer is colon cancer. In other embodiments, the type of cancer may be breast cancer, skin cancer, thyroid cancer, prostate cancer, kidney cancer, pancreatic cancer, lung cancer, bladder cancer, rectal cancer, or leukemia.

In another embodiment, the first subcellular compartment is a nuclear compartment and the second subcellular compartment is a cytoplasmic compartment. In another embodiment, the first and second subcellular compartments refer to any of a number of other subcellular compartments including but not limited to cell membrane, endoplasmic reticulum, golgi, lysosomes, and/or any compartment that can be labeled molecularly.

In one embodiment, the quantity of the particular biomarker present within the first and the quantity of the particular biomarker present within the second subcellular compartments is each determined using an automated pathology system.

This invention also provides a method for determining the likelihood a particular therapy will be successful for a patient afflicted with a type of cancer comprising (a) determining a quantity of a particular biomarker present within a first subcellular compartment and a quantity of such biomarker present within a second subcellular compartment in such cells of interest present in a tissue sample from the patient; (b) obtaining a ratio of the quantity of the biomarker present within the first subcellular compartment relative to the quantity of the particular biomarker present within the second subcellular compartment; and (c) comparing the ratio so obtained to a plurality of standard reference ratios associated with responsiveness and nonresponsiveness of cells of such type of cancer to treatment with the particular therapy, wherein the likelihood of success of the particular therapy is determined based on the reference ratio numerically closest to the ratio obtained.

In one embodiment, the particular biomarker is thymidylate synthase.

In another embodiment, the type of cancer is colon cancer. In other embodiments, the type of cancer may be breast cancer, skin cancer, thyroid cancer, prostate cancer, kidney cancer, pancreatic cancer, lung cancer, bladder cancer, rectal cancer, or leukemia.

In another embodiment, the first subcellular compartment is a nuclear compartment and the second subcellular compartment is a cytoplasmic compartment. In another embodiment, the first and second subcellular compartments refer to any of a number of other subcellular compartments including but not limited to cell membrane, endoplasmic reticulum, golgi, lysosomes, and/or any compartment that can be labeled molecularly.

In one embodiment, the quantity of the particular biomarker present within the first and the quantity of the particular biomarker present within the second subcellular compartments is each determined using an automated pathology system.

The present invention provides kits for practice of the afore-described methods. The invention provides a kit comprising (a) a first stain specific for thymidylate synthase; (b) a second stain specific for a first subcellular compartment of a cell; (c) a third stain specific for a second subcellular compartment of a cell; and (d) instructions for using the kit.

In one embodiment, the kit further comprises standard reference ratios of nuclear/cytoplasmic thymidylatesynthase levels in cells associated with survival, stage of disease, or response to therapy.

In another embodiment, the second stain is specific for a nuclear compartment and the third stain is specific for a cytoplasmic compartment. In another embodiment, the first and second subcellular compartments can refer to any of a number of other subcellular compartments including but not limited to cell membrane, endoplasmic reticulum, golgi, lysosomes, and/or any compartment that can be labeled molecularly.

In another embodiment, the stains are fluorescent stains.

In certain embodiments, kits may comprise an antibody against TS, a reagent to label cytoplasm in cells, a reagent to label nuclei in cells and further reagents to detect each of these. This kit may also contain a reagent to differentiate tumor from stroma detection means. In certain embodiments, kits may comprise antibodies against TS and/or any of other colon cancer markers including but not limited to epidermal growth factor receptor (EGFR), HER1, HER 2, HER3, HER4, defensin alpha6, Pms2, SZ-Catenin, CTNNB1, LRP5, GSK3SZ, Axin-1, CtBP1, CD137/CD137L, BCRP/ABCG2, CD80 (B7-1), CD86 (B7-2), ALCAM, CKB, hnRNP F, E-cadherin, beta-catenin and CD-44v6, Ep-CAM, bcl-2, p53, Ki-67, cyclin D1, carcinoembryonic antigen, neuropilin (NRP), PIK3Ca, c-myc p64, c-myc p67, CYP1B1, aryl hydrocarbon receptor (AhR), PRL-1, PRL-2, PRL-3, Tenascin C, TUCAN, glucose-regulated protein 78, aberrant cytochrome c oxidase subunit I, and/or Galectin-3. In other embodiments, a kit may comprise appropriate reagents for determining the level of protein activity in the cells of a subject.

In still other embodiments, a kit may comprise a microarray comprising probes of TS and/or any of other colon cancer markers including but not limited to epidermal growth factor receptor (EGFR), HER1, HER 2, HER3, HER4, defensin alpha6, Pms2, SZ-Catenin, CTNNB1, LRP5, GSK3SZ, Axin-1, CtBP1, CD137/CD137L, BCRP/ABCG2, CD80 (B7-1), CD86 (B7-2), ALCAM, CKB, hnRNP F, E-cadherin, beta-catenin and CD-44v6, Ep-CAM, bcl-2, p53, Ki-67, cyclin D1, carcinoembryonic antigen, neuropilin (NRP), PIK3Ca, c-myc p64, c-myc p67, CYP1B1, aryl hydrocarbon receptor (AhR), PRL-1, PRL-2, PRL-3, Tenascin C, TUCAN, glucose-regulated protein 78, aberrant cytochrome c oxidase subunit I, and/or Galectin-3 genes, mRNA, or proteins. A kit may comprise one or more probes or primers for detecting the expression level of these biomarkers and/or a solid support on which probes are attached and which may be used for detecting expression. A kit may further comprise controls, buffers, and instructions for use.

Kits may also comprise a library of nuclear TS expression levels or nuclear/cytoplasmic TS ratios associated with survival, response to therapy, stage of disease, etc., e.g., reference sets.

In one embodiment, the kit comprises a computer readable medium on which is stored one or more nuclear TS expression levels or nuclear/cytoplasmic TS ratios, AQUA® scores, or other measures of gene expression associated with survival, response to therapy, stage of disease, etc., or at least values representing nuclear TS levels or nuclear/cytoplasmic TS ratios, AQUA® scores, or other measures of gene expression associated with survival, response to therapy, stage of disease, etc. The kit may comprise ratio analysis software capable of being loaded into the memory of a computer system.

Kit components may be packaged for either manual or partially or wholly automated practice of the foregoing methods. In other embodiments involving kits, this invention contemplates a kit including compositions of the present invention, and optionally instructions for their use. Such kits may have a variety of uses, including, for example, imaging, diagnosis, therapy, and other applications.

The present invention provides, among other things, methods and compositions for diagnosing, prognosing and treating colon cancer. While specific embodiments of the subject invention have been discussed, the specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

The present invention provides for methods of diagnosing, prognosing, or staging colon cancer in a subject, comprising determining the level of nuclear TS expression or a nuclear/cytoplasmic TS ratio in a cell of a subject, wherein the level of nuclear TS or a ratio of nuclear/cytoplasmic TS indicates the degree of survival.

The present invention also provides for methods of selecting and evaluating therapies for cancer, particularly colon cancer, that comprise quantitatively evaluating in biological samples, particularly in tissue samples, the amount of TS localized in nuclear compartment(s) or the ratio of the amount of TS localized in nuclear compartment(s) to the amount of TS localized in cytoplasmic compartment(s) (i.e. the nuclear/cytoplasmic TS ratio). In the instance when a ratio is measured, the methods allow internal standardization and normalization and can reveal biologically significant relationships that may be obscured when evaluated by subjective means such as common immunohistochemistry or by biological sample preparation. Evaluation of nuclear or a nuclear/cytoplasmic TS ratio in biological samples may also comprise methods of diagnosing, staging and prognosing colon cancer.

The present invention further provides quantitative multiplex assays for selecting and evaluating therapies for colon cancer. The ability to multiplex markers allows for greater complexity in the assessment of multiple biomarkers that can contribute to predicting patient outcome. The quantitative multiplex assays may also comprise methods of diagnosing, staging and prognosing colon cancer. The nuclear TS level or the nuclear/cytoplasmic TS ratio assay may be performed in conjunction with any of the multiplex assays.

The present invention also provides for compositions and kits for the practice of the methods described in the invention. These embodiments of the present invention, other embodiments, and their features and characteristics will be apparent from the description and claims that follow.

The following Experimental Details are set forth to aid in an understanding of the subject matter of this disclosure, but are not intended to, and should not be construed to, limit in any way the claims which follow thereafter.

Experimental Details

Part I

A. Methods of Determining the Nuclear or the Nuclear/Cytoplasmic TS Ratio and/or the Expression of Colon Cancer Markers Quantitative protein expression and localization analysis of TS in colon cancer tumors reveals that the nuclear levels or the nuclear to cytoplasmic ratio, is significantly associated with survival. Both nuclear expression (p=0.03) and nuclear:cytoplasmic ratio (p=0.04) are independent predictors of survival by multivariate analysis with stage, age at diagnosis, gender and race. Taken together, these data suggest that subcellular localization of TS is critical for prediction of outcome in colon cancer. Furthermore, a ratio of nuclear to cytoplasmic expression appears to be a novel biomarker for predicting survival, and perhaps predicting response to therapy, such as chemotherapy. Accordingly, provided herein are methods of diagnosing, prognosing, and/or staging colon cancer in a subject, comprising determining nuclear TS levels or nuclear/cytoplasmic TS ratio in a cell of said subject. The determined level or ratio indicates the presence or stage of colon cancer in a subject, or the prognosis for survival of said patient, wherein a ratio of greater than one indicates decreased survival.

Also provided herein are methods for evaluating colon cancer therapies such as chemotherapies comprising the determination of nuclear TS levels or nuclear/cytoplasmic TS ratio in a cell of a subject having colon cancer.

In one embodiment, a method of determining whether a subject having colon cancer is likely to respond to a colon cancer therapy, or for determining whether more aggressive therapy is required, comprises determining the amount of TS localized in the nucleus, or the ratio of the amount of TS localized in the nucleus to the amount of TS localized in the cytoplasm in a cell of said subject, wherein the nuclear levels or determined ratio indicates whether the subject is likely to respond to the colon cancer therapy. The colon cancer therapy may be selected, for example, from the group consisting of: target-based therapy, chemotherapy and hormone therapy.

In another embodiment, a method of selecting a colon cancer therapy for a subject comprises determining the nuclear TS levels or the nuclear/cytoplasmic TS ratio in a cell of said subject, wherein the nuclear levels or determined ratio indicates the appropriate therapy for the subject. In certain embodiments, the colon cancer therapy may be selected from either chemotherapy, target-based therapy or hormone therapy. The determined ratio may indicate that the subject is likely to respond to chemotherapeutic or target-based therapy but not hormone therapy, that the subject is likely to respond to hormone therapy but not target-based therapy or chemotherapy, to all therapies, or to none of these therapies.

The methods described herein comprising determining the nuclear levels or nuclear/cytoplasmic TS ratio may be practiced in a multiplex format along with other assays, e.g., on a single slide or other reaction vessel. For example, nuclear TS levels or nuclear/cytoplasmic TS ratio may be determined along with the expression of epidermal growth factor receptor (EGFR), HER family members such as HER1, HER 2, HER3 HER4, defensin alpha6, Pms2, SZ-Catenin, CTNNB1, LRP5, GSK3SZ, Axin-1, CtBP1, CD137/CD137L, BCRP/ABCG2, CD80 (B7-1), CD86 (B7-2), ALCAM, CKB, hnRNP F, E-cadherin, beta-catenin and CD-44v6, Ep-CAM, bcl-2, p53, Ki-67, cyclin D1, carcinoembryonic antigen, neuropilin (NRP), PIK3Ca, c-myc p64, c-myc p67, CYP1B1, aryl hydrocarbon receptor (AhR), PRL-1, PRL-2, PRL-3, Tenascin C, TUCAN, glucose-regulated protein 78, aberrant cytochrome c oxidase subunit I, or Galectin-3 (and any combination of such members), and/or the various multiplex assays described below, that allows both tests to be done on a single slide or multiple slides with means for standardizing measurement across slides.

In other embodiments, methods for evaluating colon cancer therapies or diagnosing, prognosing, and/or staging colon cancer comprise a multiplex determination of biomarker expression not including the determination of the nuclear levels or nuclear/cytoplasmic TS ratio or TS ratio together with total nuclear and cytoplasmic TS levels (total TS). The methods may comprise determining the expression of any combination of nuclear levels or nuclear/cytoplasmic TS ratio in conjunction with determining the expression of any colon cancer marker or markers in the art, such as those listed above. The National Center for Biotechnology Information (NCBI) accession numbers is as follows: TS: NM_001071.

Incorporated by reference in their entirety are any polynucleotide and polypeptide sequences which reference an accession number correlating to an entry in the public database of the National Center for Biotechnology Information (NCBI) on the world wide web at ncbi.nlm.nih.gov.

Biomarkers comprising a set to be used in the various multiplex assays described herein may be selected using a genetic algorithm, as further described below.

The level of expression of the various biomarkers used in the assays may be determined by quantifying the level of expression of the genes encoding the biomarkers in the cell, or it may be determined by quantifying the amounts of the biomarker proteins in the cell.

Methods for quantifying the expression level of biomarker genes and ultimately the activity of biomarker proteins are known in the art. For example, the expression level of a biomarker gene can be determined by reverse transcription-polymerase chain reaction (RT-PCR); dotblot analysis; Northern blot analysis and in situ hybridization. Alternatively, the level of a biomarker can be analyzed using an appropriate antibody. Tumor cells can be obtained using known procedures, such as a needle biopsy (See Kim, C. H. et al. *J. Virol.* 66:3879-3882 (1992)); Biswas, B. et al. *Annals NY Acad. Sci.* 590:582-583 (1990)); Biswas, B. et al. *J. Clin. Microbiol.* 29:2228-2233 (1991).

In certain embodiments, the amounts of biomarkers are determined using antibodies specific for the biomarkers.

In certain embodiments, the level of expression of the biomarkers is determined by determining the AQUA® score of nuclear and cytoplasmic TS, e.g., by using the AQUA® automated pathology system.

AQUA® (for Automated Quantitative Analysis) is a method of analysis of absolute measurement of protein expression in situ. This method allows measurements of protein expression within sub-cellular compartments that results in a number directly proportional to the number of molecules expressed per unit area. For example, to measure nuclear TS, the tissue is "masked" using cytokeratin in one channel to normalize the area of tumor and to remove the stromal and other non-tumor material from analysis. Then an image is taken using DAPI to define a nuclear compartment. The pixels within the mask and within the DAPI-defined compartment are defined as nuclear. The intensity of expression of TS is measured using a third channel. The intensity of that subset of pixels divided by the number of pixels (to normalize the area from spot to spot) gives an AQUA® score. This score is directly proportional to the number of molecules of TS per unit area of tumor. This method, including details of out-of-focus light subtraction imaging methods, is described in detail in a Nature Medicine paper (Camp, R. L., Chung, G. G. & Rimm, D. L. Automated subcellular localization and quantification of protein expression in tissue microarrays. *Nat Med* 8, 1323-7 (2002)), as well as U.S. Ser. No. 10/062,308, filed Feb. 1, 2002, both of which references are incorporated herein by their entireties.

Exemplary embodiments of the methods of the invention wherein AQUA® is used to determine, for example, the amount of cytoplasmic, nuclear, or nuclear and cytoplasmic TS and thus the nuclear TS levels or nuclear/cytoplasmic TS ratio is described in the Exemplification below.

Methods of quantitatively determining biomarker expression may comprise determining the location of the biomarkers in the cell, as well as the quantity of the biomarkers of the cell. AQUA® is an example of a method which accomplishes both of these goals.

However, other methods of quantitatively determining biomarker expression may be used instead of AQUA® analysis. For example, the location of biomarkers in a cell may be accomplished by subcellular fractionation followed by quantitation of the biomarkers, e.g. by ELISA analysis, analysis with a polypeptide array, or other method for quantifying biomarker amounts.

In some embodiments, methods of detecting the level of expression of biomarkers may comprise the use of a microarray. Arrays are often divided into microarrays and macroarrays, where microarrays have a much higher density of individual probe species per area. Microarrays may have as many as 1000 or more different probes in a 1 cm$^2$ area. There is no concrete cut-off to demarcate the difference between micro- and macroarrays, and both types of arrays are contemplated for use with the invention.

Microarrays are known in the art and generally consist of a surface to which probes that correspond in sequence to gene products (e.g., cDNAs, mRNAs, oligonucleotides, proteins) are bound at known positions. In one embodiment, the microarray is an array (e.g., a matrix) in which each position represents a discrete binding site for a product encoded by a gene (e.g., a protein or RNA), and in which binding sites are present for products of most or almost all of the genes in the organism's genome.

When fluorescently labeled probes are used, the fluorescence emissions at each site of a transcript array may be detected by scanning confocal laser microscopy. When two fluorophores are used, a separate scan, using the appropriate excitation line, is carried out for each of the two fluorophores used. Fluorescent microarray scanners are commercially available from Affymetrix, Packard BioChip Technologies, BioRobotics and many other suppliers. Signals are recorded, quantitated and analyzed using a variety of computer software.

According to the method of the invention, the relative abundance of a gene product in two cells or cell lines is scored as a perturbation and its magnitude determined (i.e., the abundance is different in the two sources of gene product tested), or as not perturbed (i.e., the relative abundance is the same). As used herein, a difference between the two sources of at least a factor of about 25% (gene product from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 2-fold to about 5-fold, but more sensitive methods are expected to be developed.

In addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In certain embodiments, the data obtained from such experiments reflects the relative expression of each gene represented in the microarray. Expression levels in different samples and conditions may now be compared using a variety of statistical methods.

Although microarrays may be used in certain embodiments, various other methods of detection of gene expression are available. This section describes a few exemplary methods for detecting and quantifying mRNA or polypeptide encoded thereby.

In one embodiment, mRNA obtained from a sample is reverse transcribed into a first cDNA strand and subjected to PCR, e.g., RT-PCR. House keeping genes, or other genes whose expression does not vary may be used as internal controls and controls across experiments. Following the PCR reaction, the amplified products may be separated by electrophoresis and detected. By using quantitative PCR, the level of amplified product will correlate with the level of RNA that was present in the sample. The amplified samples may also be separated on an agarose or polyacrylamide gel, transferred onto a filter, and the filter hybridized with a probe specific for the gene of interest. Numerous samples may be analyzed simultaneously by conducting parallel PCR amplification, e.g., by multiplex PCR.

"Dot blot" hybridization has gained wide-spread use, and many versions were developed (see, e.g., M. L. M. Anderson and B. D. Young, in *Nucleic Acid Hybridization—A Practical Approach*, B. D. Hames and S. J. Higgins, Eds., IRL Press, Washington D.C., Chapter 4, pp. 73-111, 1985).

In another embodiment, mRNA levels is determined by dot blot analysis and related methods (see, e.g., G. A. Beltz et al., in *Methods in Enzymology*, Vol. 100, Part B, R. Wu, L. Grossmam, K. Moldave, Eds., Academic Press, New York, Chapter 19, pp. 266-308, 1985). In one embodiment, a specified amount of RNA extracted from cells is blotted (i.e., non-covalently bound) onto a filter, and the filter is hybridized with a probe of the gene of interest. Numerous RNA samples may be analyzed simultaneously, since a blot may comprise multiple spots of RNA. Hybridization is detected using a method that depends on the type of label of the probe. In another dot blot method, one or more probes are attached to a membrane, and the membrane is incubated with labeled nucleic acids obtained from and optionally derived from RNA of a cell or tissue of a subject. Such a dot blot is essentially an array comprising fewer probes than a microarray.

Another format, the so-called "sandwich" hybridization, involves covalently attaching oligonucleotide probes to a solid support and using them to capture and detect multiple nucleic acid targets (see, e.g., M. Ranki et al. (1983) *Gene*, 21:77-85; A. M. Palva, et al, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R. B. Wallace et al. (1979) *Nucleic Acid Res.* 6, 11:3543; and B. J. Connor et al. (1983) *PNAS* 80:278-282). Multiplex versions of these formats are called "reverse dot blots."

mRNA levels may also be determined by Northern blots. Specific amounts of RNA are separated by gel electrophoresis and transferred onto a filter which is then hybridized with a probe corresponding to the gene of interest. This method, although more burdensome when numerous samples and genes are to be analyzed provides the advantage of being very accurate.

Another method for high throughput analysis of gene expression is the serial analysis of gene expression (SAGE) technique, first described in Velculescu et al. (1995) *Science* 270, 484-487. Among the advantages of SAGE is that it has the potential to provide detection of all genes expressed in a given cell type, provides quantitative information about the relative expression of such genes, permits ready comparison of gene expression of genes in two cells, and yields sequence information that may be used to identify the detected genes. Thus far, SAGE methodology has proved itself to reliably detect expression of regulated and nonregulated genes in a variety of cell types (Velculescu et al. (1997) *Cell* 88, 243-251; Zhang et al. (1997) *Science* 276, 1268-1272 and Velculescu et al. (1999) *Nat. Genet.* 23, 387-388.

The level of expression of a biomarker may be determined by in situ hybridization. In one embodiment, a tissue sample is obtained from a subject, the tissue sample is sliced, and in situ hybridization is performed according to methods known in the art, to determine the level of expression of the genes of interest.

In other methods, the level of expression of a biomarker is detected by measuring the level of protein encoded by biomarker gene. This may be done, e.g., by immunoprecipitation, ELISA, or immunohistochemistry using an agent, e.g., an antibody, that specifically detects the protein encoded by the gene. Other techniques include Western blot analysis. Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which may be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, may be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In the case of polypeptides which are secreted from cells, the level of expression of these polypeptides may be measured in biological fluids.

The above-described methods may be performed using cells grown in cell culture, or on cell or tissue specimens from a subject. Specimens may be obtained from an individual to be tested using either "invasive" or "non-invasive" sampling means. A sampling means is said to be "invasive" if it involves the collection of nucleic acids from within the skin or organs of an animal (including, especially, a murine, a human, an ovine, an equine, a bovine, a porcine, a canine, or a feline animal). Examples of invasive methods include blood collection, semen collection, needle biopsy, pleural aspiration, umbilical cord biopsy, etc. Examples of such methods are discussed by Kim, C. H. et al. (1992) *J. Virol.* 66:3879-3882; Biswas, B. et al. (1990) *Annals NY Acad. Sci.* 590:582-583; Biswas, B. et al. (1991) *J. Clin. Microbiol.* 29:2228-2233. It is also possible to obtain a cell sample from a subject, and then to enrich it in the desired cell type. For example, cells may be isolated from other cells using a variety of techniques, such as isolation with an antibody binding to an epitope on the cell surface of the desired cell type.

In certain embodiments, a single cell is used in the analysis. It is also possible to obtain cells from a subject and culture the cells in vitro, such as to obtain a larger population of cells from which RNA may be extracted. Methods for establishing cultures of non-transformed cells, i.e., primary cell cultures, are known in the art.

In other embodiments, the cell comprises a cell culture pellet, which may be present on a cell culture pellet microarray.

When analyzing from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA and proteins in the tissue and cells may quickly become degraded. Accordingly, in one embodiment, the cells obtained from a subject are snap frozen as soon as possible. In another embodiment, it is preferred to use material in the form that it typically is prepared and stored in standard pathology practice. Therefore in a preferred embodiment tissue sections are from formalin-fixed, paraffin embedded tissue blocks. Whole tissue sections may be used or tissue microarrays (TMAs).

Tissue microarrays, a method for analysis of display of large cohorts of cancer patients on a single slide, have been slow to be used for discovery since the analysis of these arrays has generally been subjective, thus invalidating many of the algorithms used for discovery in nucleic acid array experiments. However, tissue microarray technology enables high throughput analysis of protein expression with standardization of many variables and capacity for embedded discovery by allowing an in-situ protein assay of markers of interest on large cohorts of tumors with the inclusion of spatial subcellular localization information and multiplexed analysis.

In certain embodiments, the tissue sample is present on a microarray. Paraffin-embedded formalin-fixed specimens may be prepared using punch "biopsy" cores from tissue specimens of interest. Each core may be arrayed into a separate recipient block, and sections cut and processed, for example as previously described in Konenen, J. et al., Tissue microarrays for high-throughput molecular profiling of tumor specimens, (1987) *Nat. Med.* 4:844-7 and Chung, G. G. et al., *Clin Cancer Res.* (2001) Dec; 7(12):4013-20.

In certain embodiments, the cell comprises a tissue sample, which may be present on a tissue microarray. For example, paraffin-embedded formalin-fixed specimens may be prepared, and punch "biopsy" cores taken from separate areas of the specimens. Each core may be arrayed into a separate recipient block, and sections cut and processed as previously described, for example, in Konenen, J. et al., Tissue microarrays for high-throughput molecular profiling of tumor specimens, (1987) *Nat. Med.* 4:844-7 and Chung, G. G. et al., *Clin. Cancer Res.* (In Press).

B. Methods for Comparing Test Values with a Reference Set

Comparison to a reference set is particularly useful in applications of the above-described methods, for example when they are used in methods for diagnosing and prognosing a colon cancer in a subject, or for selecting therapeutics for a subject having colon cancer. The data obtained thereby, for example compartment specific AQUA® scores (i.e. nuclear or cytoplasmic) or a ratio (i.e. nuclear/cytoplasmic), or a ratio and total (nuclear+cytoplasmic), may further be compared to a reference set of values associated with various states of colon cancer, various treatment outcomes, survival rates, etc.

Comparison of the determined value with reference values is preferably conducted using computer systems. In one embodiment, a ratio, AQUA® scores, or other measures of protein amount are obtained in two cells and the values from the two cells are introduced into a computer system for comparison. In a preferred embodiment, one value is entered into a computer system for comparison with values that are already present in the computer system, or in computer-readable form that is then entered into the computer system.

In one embodiment, the invention provides computer readable forms of AQUA® scores, for example cytoplasmic or nuclear AQUA® scores, or nuclear/cytoplasmic AQUA® score TS ratios, or total, or other measures of protein amount.

The data may be in the form of a table, such as an Excel table. The data may be alone, or it may be part of a larger database, e.g., comprising other expression profiles. For example, the data may be part of a public database. The computer readable form may be in a computer.

In one embodiment, the invention provides methods for determining the similarity between the AQUA® score, nuclear TS levels or nuclear/cytoplasmic TS ratio, or other measure of gene expression in a first cell, e.g., a cell of a subject, and that in a second cell, comprising obtaining AQUA® scores, for example nuclear TS levels or nuclear/cytoplasmic TS ratio, or other measure of gene expression in a first cell and entering these values into a computer comprising a database including records comprising values corresponding to AQUA® scores, for example nuclear TS levels or nuclear/cytoplasmic TS ratio, or other measure of gene expression in a second cell, and processor instructions, e.g., a user interface, capable of receiving a selection of one or more values for comparison purposes with data that is stored in the computer. The computer may further comprise a means for converting the comparison data into a diagram or chart or other type of output.

In another embodiment, values representing the nuclear TS levels or nuclear/cytoplasmic TS ratio, AQUA® score, or other measure of gene expression are entered into a computer system, comprising one or more databases with reference nuclear TS levels or nuclear/cytoplasmic TS ratios, AQUA® scores, or other measures of protein amount obtained from more than one cell. For example, a computer may comprise expression data of diseased and normal cells. Instructions are provided to the computer, and the computer is capable of comparing the data entered with the data in the computer to determine whether the data entered is more similar to that of a normal cell or of a diseased cell.

In another embodiment, the computer comprises the nuclear TS AQUA® score or nuclear/cytoplasmic TS ratio, or total TS, or other measure of gene expression in cells of subjects at different stages of colon cancer and the computer is capable of comparing the nuclear TS levels or nuclear/cytoplasmic TS ratio, AQUA® score, or other measure of gene expression entered into the computer with the data stored, and produce results indicating to which of the nuclear TS levels or nuclear/cytoplasmic TS ratio, AQUA™ score, or other measure of gene expression in the computer, the one entered is most similar to the determined nuclear TS levels or nuclear/cytoplasmic TS ratio, AQUA® score, or other measure of protein amount, such as to determine the stage of cancer in the subject.

In yet another embodiment, the reference expression profiles in the computer are the nuclear TS levels or nuclear/cytoplasmic TS ratio, AQUA® score, or other measure of gene expression from cells of one or more subjects having colon cancer, which cells are treated in vivo or in vitro with a drug used for therapy of colon cancer. Upon entering the nuclear TS level or nuclear/cytoplasmic TS ratio, AQUA® score, or other measure of gene expression of a cell of a subject treated in vitro or in vivo with the drug, the computer is instructed to compare the data entered to the data in the computer, and to provide results indicating whether the data input into the computer are more similar to those of a cell of a subject that is responsive to the drug or more similar to those of a cell of a subject that is not responsive to the drug. Thus, the results indicate whether the subject is likely to respond to the treatment with the drug or unlikely to respond to it.

In one embodiment, the invention provides systems comprising a means for receiving the nuclear TS levels or nuclear/cytoplasmic TS ratio, AQUA® score, or other measure of gene expression for one or a plurality of samples; a means for comparing the nuclear TS levels or nuclear/cytoplasmic TS ratio, AQUA® score, or other measure of gene expression from each of said one or plurality of samples to a common reference frame; and a means for presenting the results of the comparison. A system may further comprise a means for clustering the data.

In another embodiment, the invention provides computer programs for analyzing the nuclear TS levels or nuclear/cytoplasmic TS ratio, AQUA® score, or other measure of gene expression comprising (a) a computer code that receives as input the nuclear TS levels or nuclear/cytoplasmic TS ratio, AQUA® score, or other measure of gene expression for a plurality of samples and (b) a computer code that compares the nuclear TS levels or nuclear/cytoplasmic TS ratio, AQUA® score, or other measure of gene expression from each of said plurality of samples to a common reference frame.

The invention also provides machine-readable or computer-readable media including program instructions for performing the following steps: (a) comparing a plurality of values corresponding to the nuclear TS levels or nuclear/cytoplasmic TS ratio, AQUA® score, or other measure of gene expression in a query cell with a database including records comprising reference nuclear TS levels or nuclear/cytoplasmic TS ratios, AQUA® scores, or other measures of protein amount of one or more reference cells and an annotation of the type of cell; and (b) indicating to which cell the query cell is most similar based on similarities of the nuclear TS levels or nuclear/cytoplasmic TS ratio, AQUA® score, or other measure of protein amount. The reference cells may be cells from subjects at different stages of colon cancer or with different prognoses, for example. The reference cells may also be cells from subjects responding or not responding to a particular drug treatment and optionally incubated in vitro or in vivo with the drug.

The reference cells may also be cells from subjects responding or not responding to several different treatments, and the computer system indicates a preferred treatment for the subject. Accordingly, the invention provides methods for selecting a therapy for a patient having colon cancer; the methods comprising: (a) providing the nuclear TS levels or nuclear/cytoplasmic TS ratio, AQUA® score, or other measure of gene expression in a diseased cell of the patient; (b) providing a plurality of reference nuclear TS levels or nuclear/cytoplasmic TS ratios, AQUA® scores, or other measures of protein amount, each associated with a therapy, wherein the subject expression profile and each reference profile has a plurality of values, each value representing a nuclear TS level or nuclear/cytoplasmic TS ratio, AQUA® score, or other measure of protein amount; and (c) selecting the reference profile most similar to the subject expression profile, to thereby select a therapy for said patient. In a preferred embodiment, step (c) is performed by a computer. The most similar reference profile may be selected by weighing a comparison value of the plurality using a weight value associated with the corresponding expression data.

A computer readable medium may further comprise a pointer to a descriptor of a stage of colon cancer or to a treatment for colon cancer.

In operation, the means for receiving the nuclear TS levels or nuclear/cytoplasmic TS ratio, AQUA® score, or other measure of protein amount, the means for comparing the nuclear TS levels or nuclear/cytoplasmic TS ratio, AQUA® score, or other measure of protein amount, the means for presenting, the means for normalizing, and the means for clustering within the context of the systems of the present invention may involve a programmed computer with the respective functionalities described herein, implemented in hardware or hardware and software; a logic circuit or other component of a programmed computer that performs the operations specifically identified herein, dictated by a computer program; or a computer memory encoded with executable instructions representing a computer program that may cause a computer to function in the particular fashion described herein.

Those skilled in the art will understand that the systems and methods of the present invention may be applied to a variety of systems, including IBM®-compatible personal computers running MS-DOS® or Microsoft Windows®.

Exemplary diagnostic tools and assays are set forth below, which comprise the above-described methodology.

In one embodiment, the invention provides methods for determining whether a subject has or is likely to develop colon cancer, particularly metastatic colon cancer, comprising determining the nuclear TS levels or nuclear/cytoplasmic TS ratio, AQUA® score, or other measure of gene expression in a cell of the subject and comparing the nuclear TS levels or nuclear/cytoplasmic TS ratio, AQUA® score, or other measure of gene expression with the nuclear TS levels or nuclear/cytoplasmic TS ratio, AQUA® score, or other measure of gene expression in a diseased cell of a subject, such that a similar nuclear TS level or nuclear/cytoplasmic TS ratio, AQUA® score, or other measure of gene expression is indicative that the subject has or is likely to develop colon cancer, particularly metastatic colon cancer. In a preferred embodiment, the cell is essentially of the same type as that which is diseased in the subject.

In another embodiment the nuclear TS levels or nuclear/cytoplasmic TS ratio, AQUA® score, or other measure of gene expression may be used to confirm that a subject has a specific type or stage of colon cancer, and not a related disease or disease with similar symptoms. This may be important, in particular, in designing an optimal therapeutic regimen for the subject. Such distinction is known in the art as "differential diagnosis".

In yet another embodiment, the invention provides methods for determining the stage of a colon cancer. It is thought that the nuclear TS levels or nuclear/cytoplasmic TS ratio, AQUA® score, or other measure of gene expression with the stage of the disease. This could be confirmed, e.g., by analyzing the nuclear TS levels or nuclear/cytoplasmic TS ratio, AQUA® score, or other measure of gene expression in subjects having colon cancer at different stages, as determined by traditional methods. For example, the nuclear TS levels or nuclear/cytoplasmic TS ratio, AQUA® score, or other measure of gene expression of a diseased cell in subjects at different stages of the disease may be determined as described herein. Then, to determine the stage of colon cancer in a subject, the nuclear TS levels or nuclear/cytoplasmic TS ratio, AQUA® score, or other measure of gene expression in the subject is determined. A similar level of expression of the nuclear TS levels or nuclear/cytoplasmic TS ratio, AQUA® score, or other measure of gene expression between that in a subject and that in a reference profile of a particular stage of the disease, indicates that the colon cancer of the subject is at the particular stage.

Similarly, the methods may be used to determine the stage of the disease in a subject undergoing therapy such as chemotherapy, and thereby determine whether the therapy is effective. Accordingly, in one embodiment, the nuclear TS levels or nuclear/cytoplasmic TS ratio, AQUA® score, or other measure of gene expression is determined in a subject before the treatment and several times during the treatment. For example, a sample may be obtained from the subject before the beginning of the therapy and every 12, 24 or 72 hours during the therapy. Samples may also be analyzed one a week or once a month. Changes in the nuclear TS levels or nuclear/cytoplasmic TS ratio, AQUA® score, or other measure of gene expression over time and relative to diseased cells and normal cells will indicate whether the therapy is effective.

In yet another embodiment, the invention provides methods for determining the likelihood of success of a particular therapy in a subject having colon cancer. In one embodiment, a subject is started on a particular therapy, and the effectiveness of the therapy is determined, e.g., by determining the nuclear TS levels or nuclear/cytoplasmic TS ratio, AQUA® score, or other measure of gene expression in a cell of the subject. A normalization of the nuclear TS levels or nuclear/cytoplasmic TS ratio, AQUA® score, or other measure of gene expression, indicates that the treatment should be effective in the subject.

Prediction of the outcome of a treatment in a subject may also be undertaken in vitro. In one embodiment, cells are obtained from a subject to be evaluated for responsiveness to the treatment, and incubated in vitro with the therapeutic drug. The nuclear TS levels or nuclear/cytoplasmic TS ratio, AQUA® score, or other measure of gene expression is then measured in the cells and these values are compared to the nuclear TS levels or nuclear/cytoplasmic TS ratio, AQUA® score, or other measure of gene expression in a cell which is the normal counterpart cell of a diseased cell. The nuclear TS levels or nuclear/cytoplasmic TS ratio, AQUA® score, or other measure of gene expression may also be compared to that in a normal cell. The comparative analysis is preferably conducted using a computer comprising a database of the nuclear TS levels or nuclear/cytoplasmic TS ratio, AQUA® score, or other measure of gene expression as described above. Nuclear TS levels or nuclear/cytoplasmic TS ratio, AQUA® score, or other measure of gene expression ratio in the cells of the subject after incubation with the drug that is similar to the nuclear TS levels or nuclear/cytoplasmic TS ratio, AQUA® score, or other measure of gene expression in a normal cell and different from that in a diseased cell is indicative that it is likely that the subject will respond positively to a treatment with the drug. On the contrary, nuclear TS levels or a nuclear/cytoplasmic TS ratio, AQUA® score, or other measure of gene expression in the cells of the subject after incubation with the drug that is similar to the nuclear TS levels or nuclear/cytoplasmic TS ratio, AQUA® score, or other measure of gene expression in a diseased cell and different from that in a normal cell is indicative that it is likely that the subject will not respond positively to a treatment with the drug.

Since it is possible that a drug does not act directly on the diseased cells, but is, e.g., metabolized, or acts on another cell which then secretes a factor that will effect the diseased cells, the above assay may also be conducted in a tissue sample of a subject, which contains cells other than the diseased cells. For example, a tissue sample comprising diseased cells is obtained from a subject; the tissue sample is incubated with the potential drug; optionally one or more diseased cells are isolated from the tissue sample, e.g., by microdissection or Laser Capture Microdissection (LCM, see infra); and the nuclear expression or nuclear/cytoplasmic TS ratio is examined.

The invention may also provide methods for selecting a therapy for colon cancer for a patient from a selection of several different treatments. Certain subjects having colon cancer may respond better to one type of therapy than another type of therapy. In a preferred embodiment, the method comprises comparing the nuclear TS expression AQUA® score or the nuclear/cytoplasmic TS ratio, or other measure of gene expression in the patient with that in cells of subjects treated in vitro or in vivo with one of several therapeutic drugs, which subjects are responders or non responders to one of the therapeutic drugs, and identifying the cell which has the most similar nuclear TS expression AQUA® score or nuclear/cytoplasmic TS ratio, or other measure of gene expression to that of the patient, to thereby identify a therapy for the patient. The method may further comprise administering the therapy identified to the subject.

Part II

EXEMPLIFICATION

The present invention is further illustrated by the following examples which should not be construed as limiting in any way.

Example 1

AQUA® Based Analysis of Thymidylate Synthase (TS) within Subcellular Compartments Reveals a Novel Biomarker for Prediction of Survival in Colorectal Carcinomas AQUA® analysis, a new method for in situ determination of protein concentrations within subcellular compartments was used to assess the prognostic value of TS expression as a function of subcellular localization. A cohort [n=518] of patients with colon cancer diagnosed between 1970 and 1981 retrospectively collected from the Yale Pathology archives was examined using the tissue microarray format. X-tile was used for selection of optimal cut-points for continuous data on a test set representing one-third of the cohort, then this cut-point was applied on a validation set representing the remaining two-thirds. High nuclear expression (40% of the population) had a decrease in five-year disease-specific survival from 70 to 51% (validation set p=0.026) while patients with high cytoplasmic expression had a decrease in survival from 70 to 58% (validation set p=0.038). By Cox univariate analysis using these validated cutpoints, nuclear TS expression [risk ratio (RR)=1.46 (95% CI: 1.13-1.89; p=0.004)] is also a better predictor of overall survival compared to cytoplasmic expression [RR=1.32 (95% CI: 1.02-1.70; p=0.030)]. Using quantitative AQUA analysis data, ratio was generated between nuclear and cytoplasmic expression levels. A high nuclear:cytoplasmic ratio shows decreased survival by Kaplan-Meier analysis [65 to 45%; validation set p=0.010)] and by Cox univariate analysis [RR=1.61 (95% CI: 1.09-2.37; p=0.012)]. This ratio is independent of nuclear expression (Spearman's rho=−0.036; p=0.41) suggesting there is a unique population of patients having decreased survival that can be identified based on this ratio. Among the population with high nuclear:cytoplasmic expression, only 45% of cases were represented in the high nuclear population. Both nuclear expression (p=0.03) and nuclear:cytoplasmic ratio (p=0.04) are independent predictors of survival by multivariate analysis with stage, age at diagnosis, gender and race. Taken together, these data suggest that subcellular localization of TS is critical for prediction of outcome in colon cancer. Furthermore, a ratio of nuclear to cytoplasmic expression appears to be a novel biomarker for predicting survival, and perhaps predicting response to therapy.

Example 2

Localization of Thymidylate Synthase (TS) Expression is Prognostic for Recurrence in Two Cohorts of Over 1000 Colorectal Carcinomas Synopsis Background: Increased thymidylate synthase (TS) expression is a marker for decreased survival and response to therapy in colon cancer. TS localizes to both the nucleus and cytoplasm, but how the relationship of these expression levels affects colon cancer outcome has yet to be determined. Methods: Using AQUA® analysis, we assessed prognosis of TS expression as a function of subcellular localization on two retrospective cohorts of colorectal carcinoma. We used the first cohort (n=663) as a training set, subsequently validating optimal expression cutpoints on the second cohort (n=447). Results: A significant association between decreased five-year disease-specific survival and increased nuclear expression [16% decreased survival (72 to 56%) for the top 60% of nuclear expressing tumors (p<0.001)] and cytoplasmic expression [12% decreased survival (70 to 58%) for the top 54% of cytoplasmic expressing tumors (p=0.02)] was observed for the training set. A higher nuclear-to-cytoplasmic ratio also significantly correlated with decreased survival [15% decreased survival (66 to 51%) for the top 19% of tumors (p<0.001)]. Applying these findings to the validation set, as a function of time to recurrence, only the ratio [p=0.03 (expression ratio); p=0.182 (nuclear); p=0.710 (cytoplasmic)] showed a significant association with decreased time to recurrence. Additionally, the expression ratio significantly added to the prognostic value given by T-stage and nodal status. Conclusions: These data suggest only the relationship of nuclear to cytoplasmic TS expression, not nuclear or cytoplasmic expression alone, to be a particularly strong predictor of colon cancer survival.

Introduction

Thymidylate synthase (TS) catalyzes the reductive methylation of deoxyuridylate in the pathway for production of dTTP which is critical for DNA synthesis (1). TS expression as a determinant of sensitivity to fluoropyrimidines has been demonstrated in vitro (2, 3) and TS expression in vivo may play an important role in determining tumor response to 5'FU (4, 5). TS has been suggested to be both prognostic (6, 7) and predictive of response to therapy (see (8) for review). However, there exists considerable heterogeneity with respect to percent positivity within the population as well as variability in the literature with respect to overall prognostic value of TS expression (9). This variability is mostly likely due to differences in methodologies including differential definitions of TS positivity as determined by subjective assessment of expression levels by traditional immunohistochemical (IHC) techniques. Studies measuring mRNA have removed considerable subjectivity, but have still failed to become part of the routine practice for management of colon cancer (5, 10, 11)

Recently, it has been demonstrated that TS may have other cellular functions, including translational regulation (see (12) for review). Thus the subcellular localization of expression may be an important determinant of the functional role of TS. Due to the potential importance of and functional consequence TS sub-cellular localization, we wished to examine the role of TS localization as a function of survival. A method of automated quantitative analysis (AQUA®) was recently developed that allows for rapid analysis of immunofluorescence on tissue samples (13). This method yields a quantitative result comparable to an ELISA assay but it can measure levels of protein within user-defined subcellular compartments (14). It reduces the amount of human variability in scoring immunohistochemical staining by eye and results in a continuous range of protein expression AQUA scores rather than those on an ordinal scale (0, +1, +2, and +3). It has been widely used for a range of studies including efforts to assess outcome as a function of the subcellular localization of expression of targets of interest (15). Here, TS expression was examined, within nuclear and cytoplasmic compartments, on two independent cohorts representing over 1000 colorectal cancer specimens in tissue microarray format.

Materials and Methods

Tissue Microarray Design and Processing

TMAs containing 599 primary colorectal carcinomas (CRCs) and 477 primary colorectal carcinomas for training and validation cohorts respectively (formalin fixed, paraffin-embedded tumor samples obtained at Yale University-New Haven Hospital from 1970-1981 and across multiple sites from 1989-1996 for the validation set) were constructed at the Yale University Tissue Microarray Facility and the University of Virginia TMA facility, respectively. The validation set is the NCI Colon Cancer TMA, and was designed by statisticians at the National Cancer Institute and intended for public distribution in an effort led by Lisa McShane and others. Represented on the TMA are colon cancer specimens obtained from incident cases that occurred in members of the Kaiser Permanente Northwest Health Plan, 1989-1996.

Each tumor sample was marked for areas of invasive carcinoma and 0.6 mm cores were taken. Each core was arrayed into recipient blocks in a 1 mm-spaced grid, and 5-micron thick sections were cut and processed as previously reviewed and described (16, 17).

Immunohistochemistry

In brief, pre-cut paraffin-coated tissue microarray slides were de-paraffinized and antigen-retrieved by pressure-cooking. Slides were pre-incubated with 0.3% bovine serum albumin in 0.1M tris-buffered saline (pH 8.0) (BSA/TBS) for 60 min at room temperature. Slides were then incubated with primary antibodies against thymidylate synthase (mouse monoclonal clone TS106; 1:100 dilution; LabVision Neo-Markers, Fremont, Calif.) and pan-cytokeratin (rabbit polyclonal, 1:100 dilution, DAKO, Carpinteria, Calif.) diluted in BSA/TBS overnight at 4° C. Slides were washed 3×10 min with 1×TBS containing 0.05% Tween-20. Corresponding secondary antibodies were applied for 1 h at room temperature in BSA/TBS. These included either antibodies directly conjugated to a fluorphore for anti-cytokeratin (Alexa 488-conjugated goat anti-rabbit; 1:100, Molecular Probes, Eugene, Oreg.), and/or conjugated to a horseradish peroxidase (HRP) for anti-thymidylate synthase (DAKO, Carpinteria, Calif.). Slides were again washed 3×10 min with TBS containing 0.05% Tween-20. Slides were incubated with a fluorescent chromagen (Cy-5-tyramide, NEN Life Science Products, Boston, Mass.) which, like DAB, is activated by HRP and results in the deposition of numerous covalently associated Cy-5 dyes immediately adjacent to the HRP-conjugated secondary antibody. Cy-5 (red) was used because its emission peak is well outside the green-orange spectrum of tissue auto-fluorescence. Slides for automated analysis were cover slipped with an anti-fade DAPI-containing mounting medium (ProLong Gold, Molecular Probes, Eugene, Oreg.).

Image Acquisition

Automated image capture was performed by the AQUA® system which has previously been described in detail and reviewed (13, 18). Using an Olympus BX51 microscope, images of the cytokeratin staining visualized with Cy3, DAPI, and target staining with Cy5 were taken and saved for every histospot on the array. In and out-of-focus images were taken for each channel for future use with the AQUA® script and validation program.

AQUA® Analysis (RESA/PLACE Algorithms)

AQUA® analysis was performed as previously described (13). In brief, a tumor-specific mask is generated by thresholding the image of a marker (cytokeratin) that differentiates tumor from surrounding stroma and/or leukocytes. This creates a binary mask (each pixel is either 'on' or 'off'. Thresholding levels were verified by spot-checking a few images and then automated for the remaining images. All subsequent image manipulations involve only image information from the masked area. Next, two images (one in-focus, one slightly deeper) are taken of the compartment-specific tags and the target marker. A percentage of the out-of-focus image is subtracted from the in-focus image, based on a pixel-by-pixel analysis of the two images (an algorithm called RESA (for rapid exponential subtraction algorithm) RESA also enhances the interface between areas of higher intensity staining and adjacent areas of lower intensity staining, allowing more accurate assignment of pixels of adjacent compartments. Finally, the PLACE algorithm assigns each pixel in the image to a specific subcellular compartment. Pixels that cannot be accurately assigned to a compartment to within a user-defined degree of confidence are discarded. Pixels where the nuclear and membrane pixel intensities are too similar to be accurately assigned are negated (usually comprising <8% of the total pixels). A third compartment (the cytoplasm) can be defined by exclusion (non-membrane, non-nuclear). Once each pixel is assigned to a subcellular compartment (or excluded as described above), the signal in each location is added up. This data is saved and can subsequently be expressed either as a percentage of total signal or as the average signal intensity per compartment area. The score is expressed on a scale of 1 to 1000 as the total intensity detectable in a pixel range from 1-255 creating 3 significant figures. In this study, TS nuclear, cytoplasmic, and the ratio of nuclear to cytoplasmic signal was analyzed. Scores were adjusted according to amount of area covered by the subcellular compartments within the masked area.

Data Analysis

Histospots containing <10% tumor, as by mask area (automated), were excluded from further analysis. AQUA® scores were normalized on a 0-100 scale for each cohort by dividing by the max AQUA® score. For survival analysis, optimal cutpoints were selected using X-Tile™ as described previously (19). Monte-Carlo simulations were employed to adjust for multiple looks in optimal cut-point selection (20). Hazard ratios were assessed using the univariate and multivariate Cox-proportional hazards model (Log-rank test at alpha=0.05) employing optimal cutpoints as determined by X-tile™. Statistical analyses, including generation of Kaplan-Meier curves based on X-tile cutpoints, Cox regression and linear regression models, were performed using SPSS v14.01 (SPSS, Inc., Chicago, Ill.) and R (GNU, Boston, Mass.).

Results

To quantitatively assess TS expression in colon cancer using AQUA®, two large independent retrospective cohorts of colorectal carcinomas were obtained, each annotated with demographic, clinical, and follow-up information. For the purpose of this study, the first cohort (n=599; median disease-specific survival: 23 months) was used as a training set. The second cohort (n=447; median recurrence-free survival: 20 months) was used as a validation set to corroborate findings with the training set. Demographic and clinical make-up of each cohort is provided in Table I.

TABLE 1

Clinicopathological features of colorectal cancer (CRC) cohorts

| | Training Set (Yale) | Validation Set (NCI) |
|---|---|---|
| TOTAL | 599 | 477 |
| Median Survival (months) | 23 (disease-specific death) | 20 (recurrence-free) |
| Variable | N (%) | N (%) |
| AGE (median) | | |
| <68: 301 (50.3) | | <70: 234 (49.1) |
| >68: 291 (48.6) | | >70: 209 (43.8) |
| GENDER | | |
| Female | 328 (54.7) | 234 (49.1) |
| Male | 264 (44.1) | 208 (43.6) |
| HISTOLOGICAL GRADE | | |
| Well Differentiated | 184 (30.7) | 190 (39.8) |
| Moderately Differentiated | 230 (38.4) | 126 (26.4) |
| Poorly Differentiated | 60 (10.0) | 31 (6.5) |
| T Pathological | | |
| T1 | 20 (3.3) | 11 (2.3) |
| T2 | 181 (30.2) | 51 (10.7) |
| T3 | 313 (52.3) | 269 (56.4) |
| T4 | 3 (0.5) | 30 (6.3) |

TABLE 1-continued

Clinicopathological features of colorectal cancer (CRC) cohorts

| | Training Set (Yale) | Validation Set (NCI) |
|---|---|---|
| TOTAL | 599 | 477 |
| Median Survival (months) | 23 (disease-specific death) | 20 (recurrence-free) |
| Variable | N (%) | N (%) |
| Nodal Status | | |
| 0 lymph node metastases | 276 (46.1) | 177 (37.1) |
| 1-3 lymph node metastases | 150 (25.0) | 117 (24.5) |
| >=4 lymph node metastases | 78 (13.0) | 67 (14.1) |

The training set was constructed at the Yale Tissue Microarray facility from 599 CRC cases obtained at Yale from 1970-1981. The NCI Colon Cancer TMA (validation set) was designed by statisticians at the National Cancer Institute and constructed at the University Of Virginia Department Of Pathology. Represented on the TMA are colon cancer specimens obtained-from incident cases that occurred in members of the Kaiser Permanente Northwest Health Plan, 1989-1996. Median survival times for the training set was 23 months (disease-specific survival) and 20 months (recurrence-free survival) for the validation set. Cases are broken down by age(no information for 8 cases in training set; 32 cases in validation set), gender (no information for 7 cases in training set; 35 cases in validation set), histological grade (no information for 125 cases in training set; 130 cases in validation set), T-pathological stage (no information for 82 cases in training set; 116 cases in validation set), and nodal status (no information for 95 cases in training set; 116 cases in validation set). Percentages are given as percent total cohort.

Figure 1:
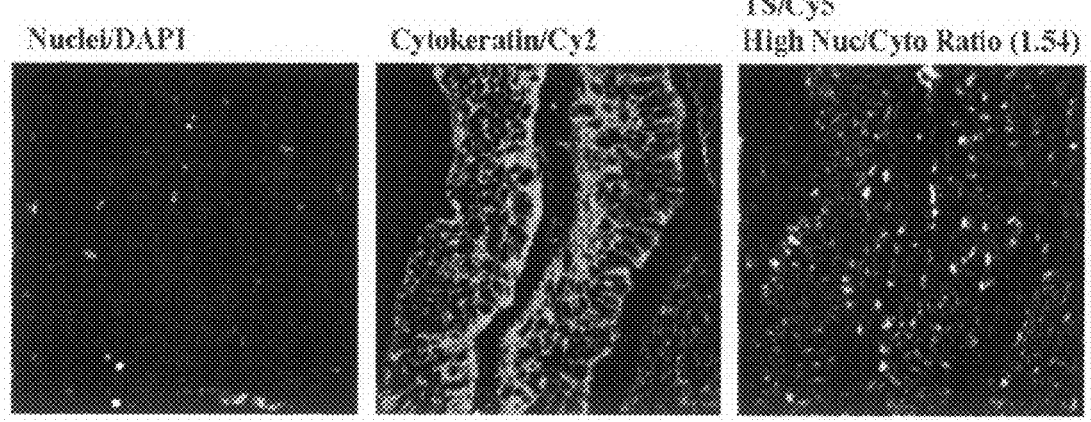
FIG. 1 are representative images of two stained colorectal tumor cores. Shown are 60× micrographs of two tissue cores representing A.) High TS expression ratio and B.) Low TS expression ratio are shown in the indicated panel. Also depicted are corresponding Dapi (delineating nuclei) and cytokeratin/cy3 (delineating tumor epithelium and cytoplasm) images.
Figure 1:
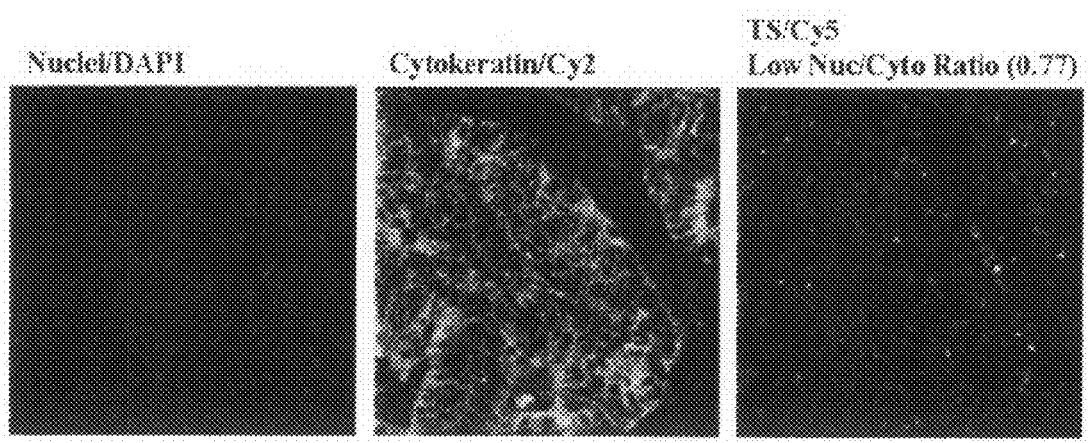

AQUA® analysis takes advantage of the multiplexing power of fluorescence staining, which allows for staining of multiple markers on a single slide. In these experiments, each tumor sample was stained for TS (Cy5), cytokeratin to differentiate epithelium from stromal components as well as to identify cytoplasm (Cy2), and DAPI to distinguish nuclei. In FIG. 1, staining patterns for each marker are given for two representative tumor samples. For each tumor sample, an AQUA® score, which is directly proportional to molecules per unit area (McCabe et al), was generated for TS expression in the nucleus and the cytoplasm. FIG. 1A shows a tumor with high nuclear TS expression relative to cytoplasm (expression ratio: 1.54) whereas FIG. 1B shows a tumor with lower nuclear expression relative to cytoplasm (expression ratio: 0.77).

Figure 2:
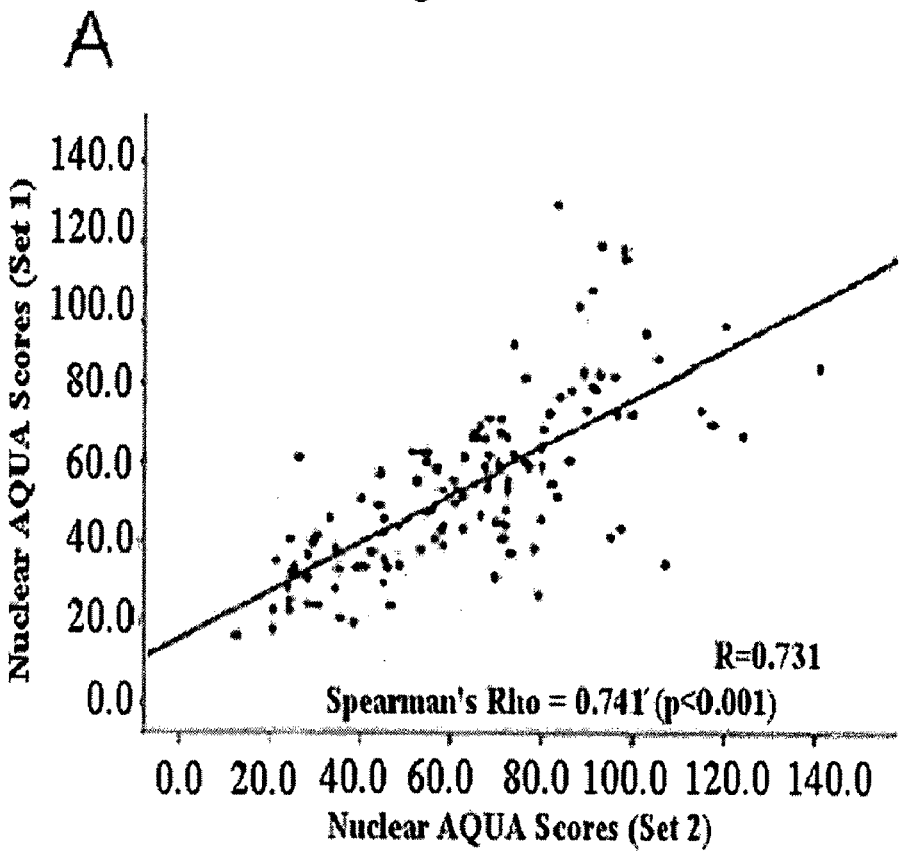
FIG. 2 is a linear regression analysis of AQUA® expression scores for redundant tissue cores.
Figure 2:
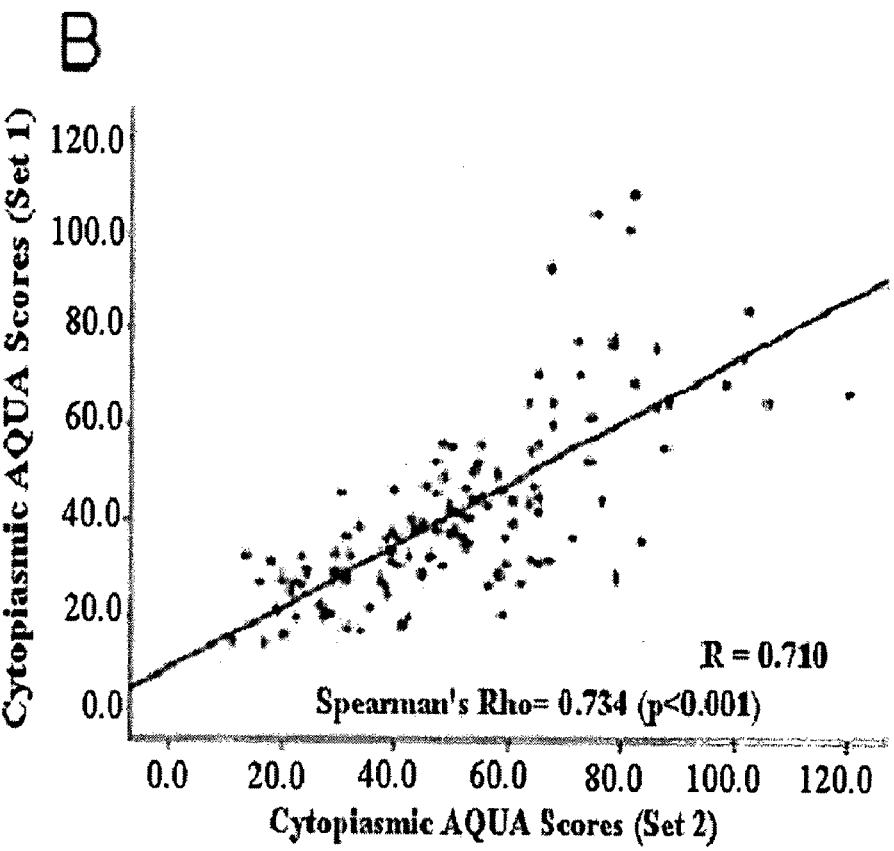
Figure 2:
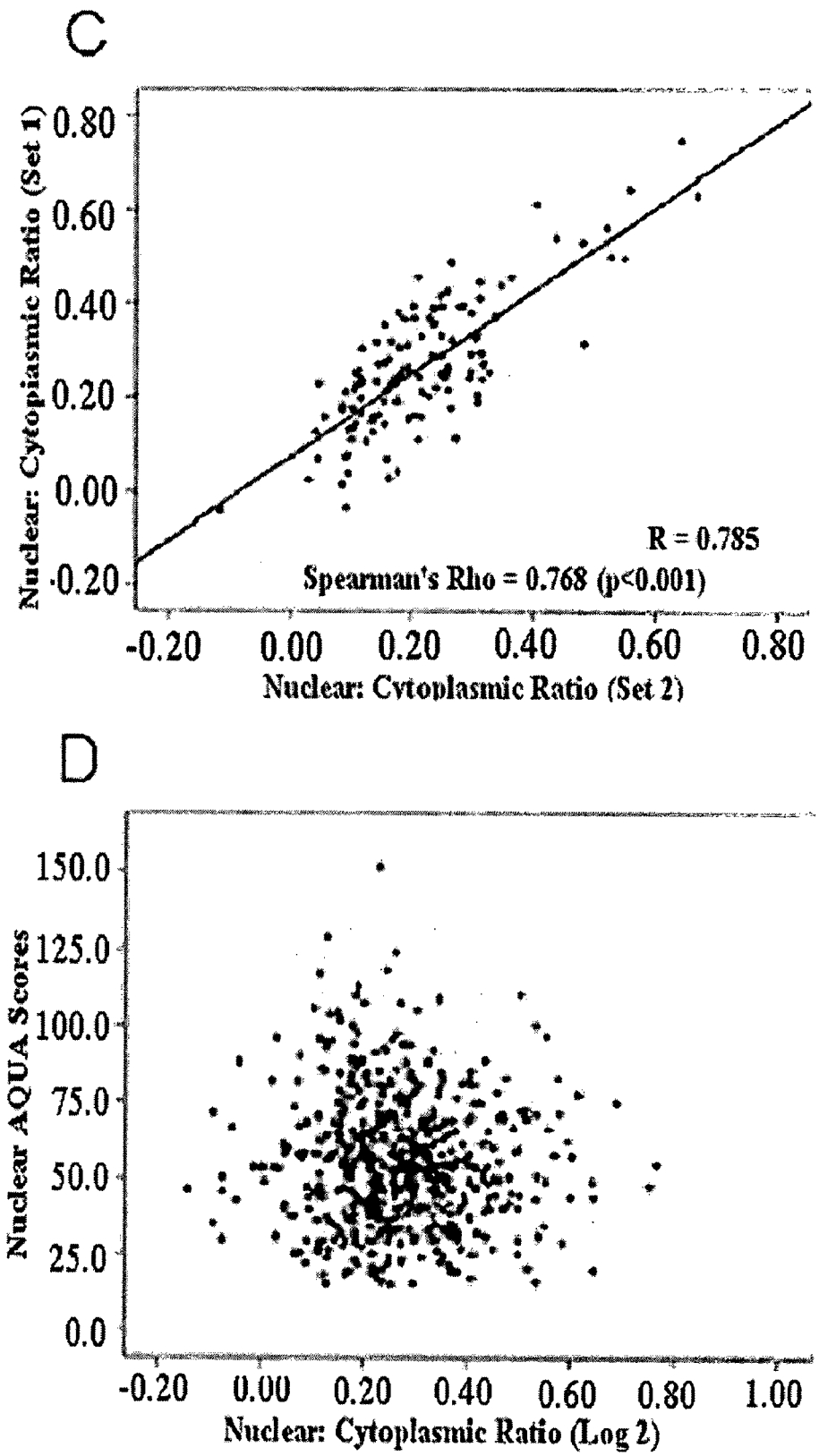

An important consideration in quantitative assays such as these is experimental reproducibility. It has been demonstrated that two tissue cores are representative of whole tumor expression in >95% of cases (21). To assess reproducibility, separate, redundant cores for 152 of the 663 tumor samples in the trainings set were stained, and then regression analysis was performed on the calculated AQUA® scores. The resulting correlation coefficients provide an assessment of not only antibody/experimental reproducibility, but also the expression heterogeneity. R-values less than 0.4 are considered experimental failures, but R-values between 0.4 and 0.8 would be considered indicative of heterogeneous marker expression, with those greater than 0.7 being considered more homogeneous. FIG. 2 shows regression analysis between nuclear (R=0.73; Spearman's Rho=0.74 (p<0.001); FIG. 2A), cytoplasmic (R=0.71; Spearman's Rho=0.73 (p<0.001); FIG. 2B), and the expression ratio (R=0.79; Spearman's Rho=0.77 (p<0.001); FIG. 2C). These results indicate high experimental reproducibility, but also indicate that TS expression within colon tumors is fairly homogenous. FIG. 2D shows regression analysis between nuclear TS expression and the expression ratio (nuclear over cytoplasmic). The lack of correlation indicates that TS expression ratio does not correlate with nuclear expression level such that patients with low level nuclear expression can still have a high expression ratio.

To observe the relationship between TS expression and patient outcome in a manner similar to that used for immunohistochemical data, but also in a rigorous manner for continuous data, it was necessary to find optimal cutpoints. A recently developed statistical method called X-tile (19) was applied to determine the optimal divisions of a continuous population. The optimal AQUA® score cutpoint for nuclear TS expression on the training set was determined to be 27.4 which represents the top 60% of the population (FIG. 3A). Patients in this group had a 16% decrease (72 to 56%) in overall five-year disease-specific survival. A significant outcome ($p<0.001$) from the Monte-Carlo simulation was observed for the optimal cutpoint using 1000 randomly generated populations. However, this cutpoint point did not show significance when applied to the NCI validation set (FIG. 3B; $p=0.182$) thus suggesting that nuclear TS expression is not a strong predictor of colon cancer outcome.

Survival analysis of cytoplasmic TS expression on the training set (FIG. 4A) also revealed a significant association between increased expression and decreased five-year disease specific survival [12% decreased survival (70 to 58%) for the top 54% of cytoplasmic expressing tumors (Monte Carlo $p=0.02$)]. However, when this cutpoint was applied to the validation set, a significant association with survival was not observed (FIG. 4B; $p=0.71$), thus suggesting that cytoplasmic TS expression is also not a strong predictor of outcome for colon cancer.

On the basis of data showing variable functional roles for TS in different subcellular compartments, a nuclear-to-cytoplasmic expression ratio for each tumor sample was generated. Ratios were log-transformed to normalize ratios less than 1 (presented here as actual ratios for ease of presentation) then analyzed as previously described. Tumors with high expression ratios greater than 1.01 (Top 19% of the population) showed a significant (Monte Carlo $p<0.001$) 15% decrease (66 to 51%) in five-year disease specific survival on the training set (FIG. 5A). This cutpoint validated ($p=0.03$) on the second cohort (FIG. 5B), suggesting that a nuclear-to-cytoplasmic ratio is a strong predictor of colon cancer outcome.

In order to ascertain whether the nuclear-to-cytoplasmic ratio adds prognostic value in colon cancer with respect to other known clinical prognostic features, Cox proportional hazards multivariate models both the training and validation set were investigated, first looking only at known clinical features common to both cohorts (T-pathological stage, nodal status, histological grade, median age at diagnosis, and gender). On the training set, the best clinical model (Table IIA) included T-pathological stage (Hazard Ratio (HR): 2.27 (95% CI: 1.56-3.29); $p<0.001$), nodal status (HR: 3.55 (95% CI: 2.38-5.39); $p<0.001$), and gender (HR: 0.71 (95% CI: 0.52-0.96); $p=0.028$). Histological grade and age at diagnosis did not make significant contributions to the model (data not shown). Application of this model to the validation set demonstrated that only T-pathological stage (HR: 2.04 (95% CI: 1.01-4.13); $p=0.049$) and nodal status (HR: 3.89 (95% CI: 2.24-6.77); $p<0.001$), but not gender (H, 0.89 (95% CI: 0.60-1.34); $p=0.589$) had significant prognostic value (Table IIB). Using the covariates, T-pathological stage and nodal status, as our best overall clinical model, the contribution of the TS expression ratio was examined (Table III). In this analysis, the optimal cutpoint was used to ascribe two groups of patients, those with a high ($>1.01$) ratio and those with a low ($<1.01$) ratio. For the training set (Table IIIA), the expression ratio (HR: 1.79 (95% CI: 1.30-2.67); $p=0.001$) makes a significant contribution to the pre-established clinical model. For the validation set, the addition of the TS expression ratio contributed prognostic significance at the 10% level (HR: 1.47 (95% CI: 0.94-2.28); $p=0.091$).

TABLE II

Multivariate analysis—Clinical Model

| Variables | Multivariate Cox Proportional Hazards | |
|---|---|---|
| | Hazard Ratio (95% CI) | p-value |
| A. Training Set | | |
| T-Path Stage (T3 and T4) | 2.27 (1.56-3.29) | <0.001 |
| Nodal Status (≧4) | 3.55 (2.38-5.39) | <0.001 |
| Gender(Female) | 0.71 (0.52-0.96) | 0.028 |
| B. Validation Set | | |
| T-Path Stage (T3 and T4) | 2.04 (1.01-4.13) | 0.049 |
| Nodal Status (≧4) | 3.89 (2.24-6.77) | <0.001 |
| Gender (Female) | 0.89 (0.60-1.34) | 0.589 |

Cox proportional hazards multivariate analysis of clinical features that produce the best clinical model. A.) Training set (5-year disease specific survival; n = 599) and B.) Validation Set (disease-free survival; n = 447) with indicated hazard ratios and p-values.

TABLE III

Multivariate analysis—Testing TS Expression Ratio

| Variables | Multivariate Cox Proportional Hazards | |
|---|---|---|
| | Hazard Ratio (95% CI) | p-value |
| A. Training Set | | |
| T-Path Stage (T3 and T4) | 2.11 (1.46-3.06) | <0.001 |
| Nodal Status (≧4) | 3.45 (2.32-5.14) | <0.001 |
| TS Nuc/Cyto Ratio >1.01 | 1.79 (1.30-2.67) | 0.001 |
| B. Validation Set | | |
| T-Path Stage (T3 and T4) | 2.06 (0.97-4.37) | 0.060 |
| Nodal Status (≧4) | 3.41 (1.88-6.17) | <0.001 |
| TS Nuc/Cyto Ratio >1.01 | 1.47 (0.94-2.28) | 0.091 |

Cox multivariate proportional hazards multivariate model adding TS expression ratio to best clinical model. A.) Training set (5-year disease specific survival; n = 599) and B.) Validation Set (disease-free survival; n = 447) with indicated hazard ratios and p-values.

Discussion

As has been seen previously, prognostic value for TS expression in colon cancer was found. However, even using an objective and strictly quantitative approach, it was found that neither the cytoplasmic nor the nuclear levels of TS validated as a prognostic marker on an independent cohort. However, it was found that TS expression is a strong predictor of colon cancer outcome as a ratio of nuclear-to-cytoplasmic expression. A 15% reduction in overall disease-specific survival in the training set was observed, then applied this expression ratio cutpoint to a second independent cohort, validating the result. Furthermore, given that time-to-recurrence in the second cohort was examined, these finding support that, not only does an expression ratio predict overall survival, but also disease-free survival. Patients with a high expression ratio had a 17% reduction in recurrence-free survival. It was also demonstrated, in a multivariate analysis, that the expression ratio adds prognostic significance to already existing clinical features used to predict survival (T-pathological stage and nodal status). Thus, a TS expression ratio represents a novel prognostic biomarker that can be used to influence decisions as to the course of treatment for patients with colorectal cancer.

The novelty of these findings also stems from the fact that the expression ratio is not dependent on overall expression levels of TS (FIG. 2D). In fact in the training set, 55% of patients in the high expression ratio group showing decreased survival were characterized as having a better prognosis when looking at total nuclear and/or cytoplasmic levels. Thus, the expression ratio provides a level of outcome prediction otherwise not afforded by measuring total cellular or sub-cellular levels of TS. Not to be bound by theory, this may be due to a number of factors, including the fact that using a ratio normalizes for individual variability or artifacts in preparation or fixation. Furthermore, these findings support a hypothesis that it is the localization of TS within tumors that contributes to poorer disease outcome, not necessarily total levels alone.

The primary role ascribed to TS is production of TTP for DNA synthesis, a process largely considered to occur in the cytoplasm (4, 22, 23). However, recent findings have shown TS to function in cellular proliferation and as an RNA binding protein where it acts as a translational repressor of several mRNAs including p53 and c-myc (see (12) for review). Although it remains unclear, nuclear localization of TS may be related to its RNA binding function. This is supported by data showing that unbound/free TS is predominantly localized in the nucleus and that it this form of TS responsible for RNA binding (24). Taken together with the data presented here, one could hypothesize that increased free TS (nuclear) relative to ternary or bound TS (cytoplasmic) is indicative of poorer outcome due to increased translational repression of key tumor suppressor genes such as p53.

As mentioned previously, increased expression of TS has been associated with decreased response to 5'FU treatment. It has also been demonstrated that increased nuclear expression is associated with decreased response to therapy (25). Preliminary evidence from the laboratory using the training set suggest that the TS expression ratio, not nuclear or cytoplasmic expression alone, significantly predicts response to 5'FU treatment as ascertained on a small subset (n=73) of patients (data not shown; insufficient informational power to validate results on second cohort). If these data can be validated on larger population of treated patients, it would demonstrate that patients with less available cytoplasmic TS relative to nuclear would have a decreased likelihood of treatment response.

Overall, these studies demonstrate that a nuclear-to-cytoplasmic expression ratio is a more powerful predictor of overall survival and disease-free survival in colorectal cancer patients than nuclear and/or cytoplasmic expression alone. As supported by multivariate analysis, this biomarker can be used with other common clinical-pathological criteria to better assess prognosis of patients in the clinic for determination of treatment course. This biomarker can also prove to be used as a potent, independent predictor for response to 5'FU treatment.

Example 3

TS Multiplexing

In order to understand the relationship between total TS expression and the nuclear:cytoplasmic ratio, the two values were regressed in both the training set and validation set (FIGS. 6A and 7A) with rank-analysis showing a weak, but significant, indirect relationship (Spearman's Rho=−0.31 (training set; p<0.001); and −0.14 (validation set; p=0.007).

To multiplex these two values for TS, the optimal cutpoints, generated in X-tile on the training set, were used to subdivide the patient population, in the training and validation set, into four distinct groups of patients: Low Total/Low Ratio, High Total/Low Ratio, Low Total/High Ratio, and High Total/High Ratio (FIG. 6A and YA). By Kaplan-Meier analysis, a statistically significant difference in five-year disease-specific survival was observed for the training set (FIG. 6B) between all groups (p<0.001), between the Low Total/Low Ratio group and the High Total/High Ratio group (p<0.001), between the Low Total/Low Ratio group and the Low Total/High Ratio group (p=0.001), and between the High Total/Low Ratio group and the High Total/High Ratio group (p=0.016). There was no significant difference in survival between the High Total/Low Ratio group and Low Total/High Ratio group. Applying these cutpoints to the validation set (FIG. 7B), a significant (10% level) difference in time-to-recurrence across all groups (p=0.056) was observed and between the Low Total/Low Ratio and High Total/High Ratio group (p=0.055). A significant difference in time-to-recurrence between the High Total/Low Ratio and High Total/High Ratio groups (p=0.021) was also observed, but not a significant difference between the Low Total/Low Ratio and Low Total/High Ratio groups (p=0.548).

These results strongly indicate an additive effect on prognosis by examining the nuclear:cytoplasmic ratio in combination with total TS expression. Importantly, these findings are validated on a second independent cohort. Given that in the second cohort, time-to-recurrence was examined, this multiplexed variable was shown not only to predict overall survival, but also disease-free survival. Previously, it was demonstrated that the nuclear:cytoplasmic ratio to be the strongest predictor of survival (HR: 1.68; 95CI: 1.23-2.3; p=0.001) compared to the other markers in univariate analysis. These findings were confirmed in the validation set (HR: 1.61; 95CI: 1.04-2.05; p=0.03). However examination of this multiplexed variable on the training set demonstrates it to be a stronger predictor of five-year disease specific survival with the High Total/High Ratio group having a hazard ratio of 3.6 (95CI: 2.1-5.9; p<0.001) compared to the Low Total/Low Ratio group. This finding was validated on the second cohort as the High Total/High Ratio group had a 2.1 hazard ratio (95CI: 0.99-4.3; p=0.055) compared to the Low Total/Low Ratio group. Taken together, these data identify a novel biomarker by which continuous expression data obtained by AQUA® analysis as both a function of total expression and a compartmental ratio can be multiplexed to produce a biomarker that is a more robust prognostic indicator than each measurement taken individually.

REFERENCES

1. Santi D V. The mechanism and structure of thymidylate synthetase. Nucleic Acids Symp Ser 1986(17):125-6.
2. Berger S H, Berger F G. Thymidylate synthase as a determinant of 5-fluoro-2'-deoxyuridine response in human colonic tumor cell lines. Mol Pharmacol 1988; 34(4):474-9.
3. Johnston P G, Drake J C, Trepel J, Allegra C J. Immunological quantitation of thymidylate synthase using the monoclonal antibody TS 106 in 5-fluorouracil-sensitive and -resistant human cancer cell lines. Cancer Res 1992; 52(16):4306-12.
4. Johnston P G, Lenz H J, Leichman C G, Danenberg K D, Allegra C J, Danenberg P V, et al. Thymidylate synthase gene and protein expression correlate and are associated with response to 5-fluorouracil in human colorectal and gastric tumors. Cancer Res 1995; 55(7):1407-12.
5. Leichman C G, Lenz H J, Leichman L, Danenberg K, Baranda J, Groshen S, et al. Quantitation of intratumoral thymidylate synthase expression predicts for disseminated colorectal cancer response and resistance to protracted-infusion fluorouracil and weekly leucovorin. J Clin Oncol 1997; 15(10):3223-9.
6. Edler D, Glimelius B, Hallstrom M, Jakobsen A, Johnston P G, Magnusson I, et al. Thymidylate synthase expression in colorectal cancer: a prognostic and predictive marker of benefit from adjuvant fluorouracil-based chemotherapy. J Clin Oncol 2002; 20(7):1721-8.
7. Edler D, Kressner U, Ragnhammar P, Johnston P G, Magnusson I, Glimelius B, et al. Immunohistochemically detected thymidylate synthase in colorectal cancer: an independent prognostic factor of survival. Clin Cancer Res 2000; 6(2):488-92.
8. Aschele C, Lonardi S, Monfardini S. Thymidylate Synthase expression as a predictor of clinical response to fluoropyrimidine-based chemotherapy in advanced colorectal cancer. Cancer Treat Rev 2002; 28(1):27-47.
9. Popat S, Matakidou A, Houlston R S. Thymidylate synthase expression and prognosis in colorectal cancer: a systematic review and meta-analysis. J Clin Oncol 2004; 22(3):529-36.
10. Leichman C G. Thymidylate synthase as a predictor of response. Oncology (Williston Park) 1998; 12(8 Suppl 6):43-7.
11. Leichman L, Lenz H J, Leichman C G, Groshen S, Danenberg K, Baranda J, et al. Quantitation of intratumoral thymidylate synthase expression predicts for resistance to protracted infusion of 5-fluorouracil and weekly leucovorin in disseminated colorectal cancers: preliminary report from an ongoing trial. Eur J Cancer 1995; 31A(7-8):1306-10.
12. Liu J, Schmitz J C, Lin X, Tai N, Yan W, Farrell M, et al. Thymidylate synthase as a translational regulator of cellular gene expression. Biochim Biophys Acta 2002; 1587(2-3):174-82.
13. Camp R L, Chung G G, Rimm D L. Automated subcellular localization and quantification of protein expression in tissue microarrays. Nat. Med. 2002; 8(11):1323-1327.
14. McCabe A, Dolled-Filhart M, Camp R L, Rimm D L. Automated quantitative analysis (AQUA) of in situ protein expression, antibody concentration, and prognosis. J Natl Cancer Inst 2005; 97(24):1808-15.
15. Berger A J, Kluger H M, Li N, Kielhorn E, Halaban R, Ronai Z, et al. Subcellular localization of activating transcription factor 2 in melanoma specimens predicts patient survival 25. Cancer Res. 2003; 63(23):8103-8107.
16. Rimm D L, Camp R L, Charette L A, Costa J, Olsen D A, Reiss M. Tissue microarray: a new technology for amplification of tissue resources. Cancer J. 2001; 7(1):24-31.
17. Rimm D L, Camp R L, Charette L A, Olsen D A, Provost E. Amplification of tissue by construction of tissue microarrays. Exp Mol Pathol 2001; 70(3):255-64.
18. Giltnane J M, Rimm D L. Technology insight: Identification of biomarkers with tissue microarray technology. Nat Clin Pract Oncol 2004; 1(2):104-11.
19. Camp R L, Dolled-Filhart M, Rimm D L. X-tile: a new bio-informatics tool for biomarker assessment and outcome-based cut-point optimization 9. Clin. Cancer Res. 2004; 10(21):7252-7259.
20. Raeside D E. Monte Carlo principles and applications. Phys Med Biol 1976; 21(2):181-97.
21. Camp R L, Charette L A, Rimm D L. Validation of tissue microarray technology in breast carcinoma 50. Lab Invest 2000; 80(12):1943-1949.
22. Kucera R, Paulus H. Localization of the deoxyribonucleotide biosynthetic enzymes ribonucleotide reductase and thymidylate synthase in mouse L cells. Exp Cell Res 1986; 167(2):417-28.
23. Johnston P G, Liang C M, Henry S, Chabner B A, Allegra C J. Production and characterization of monoclonal antibodies that localize human thymidylate synthase in the cytoplasm of human cells and tissue. Cancer Res 1991; 51(24):6668-76.
24. Bissoon-Haqqani S, Moyana T, Jonker D, Maroun J A, Birnboim H C. Nuclear expression of thymidylate synthase in colorectal cancer cell lines and clinical samples. J Histochem Cytochem 2006; 54(1):19-29.
25. Wong N A, Brett L, Stewart M, Leitch A, Longley D B, Dunlop M G, et al. Nuclear thymidylate synthase expression, p53 expression and 5FU response in colorectal carcinoma. Br J Cancer 2001; 85(12):1937-43.

What is claimed is:

1. A method of making a prognosis for a patient afflicted with colon cancer which comprises:
   a) determining a quantity of thymidylate synthase present within a first subcellular compartment and a quantity of thymidylate synthase present within a second subcellular compartment in colon cells present in a tissue sample from the patient;
   b) obtaining a ratio of the quantity of thymidylate synthase present within the first subcellular compartment relative to the quantity of the thymidylate synthase present within the second subcellular compartment; and
   c) comparing the ratio so obtained to a plurality of standard reference ratios associated with a series of prognoses so as to thereby make a prognosis for the patient;
   wherein the first subcellular compartment is a nuclear compartment and the second subcellular compartment is a cytoplasmic compartment; wherein the ratios greater than one are associated with an unfavorable prognosis for the patient;
   and wherein the ratios less than one are associated with a favorable prognosis for the patient.

2. The method of claim 1, wherein the quantity of thymidylate synthase present within the first subcellular compartment and the quantity of thymidylate synthase present within the second subcellular compartment are each determined using an automated pathology system.

3. The method of claim 1, further comprising comparing the ratio obtained to a plurality of standard reference ratios, each of which is associated with a predicted survival time, wherein the prognosis for the patient is correlated with the reference ratio numerically closest to the ratio obtained.

4. The method of claim 1, further comprising determining the relationship between (a) the ratio obtained and (b) a combined total of the quantity of thymidylate synthase present within the first subcellular compartment and the quantity of thymidylate synthase present within the second subcellular compartment and correlating the relationship so determined with the patient's prognosis.

5. The method of claim 1 wherein the ratios greater than one indicates that the patient is not likely to benefit from therapeutic treatment.

6. The method of claim 5, wherein the therapeutic treatment comprises administering a fluoropyrimidine.

7. The method of claim 6 in which the fluoropyrimidine is 5-fluorouracil (5-FU).

8. A method which comprises:
a) determining a quantity of a particular biomarker present within a first subcellular compartment and a quantity of such particular biomarker present within a second subcellular compartment in cells of interest present in a tissue sample from a patient;
b) obtaining a ratio of the quantity of the biomarker present within the first subcellular compartment relative to the quantity of the biomarker present within the second subcellular compartment; and
c) comparing the ratio so obtained to a plurality of standard reference ratios.

9. The method of claim 4, wherein a ratio obtained that is lower than one and a low combined total is associated with a favorable prognosis for the patient.

10. The method of claim 4, wherein a ratio obtained that is greater than one and a high combined total is associated with a poor prognosis for the patient.

11. The method of claim 4, wherein a ratio obtained that is greater than one and a low combined total is associated with a moderate prognosis for the patient.

12. The method of claim 4, wherein a ratio obtained that is lower than one and a high combined total is associated with a moderate prognosis for the patient.

13. The method of claim 1 wherein the ratios less than one indicate that the patient is likely to benefit from therapeutic treatment.

14. The method of claim 13, wherein the therapeutic treatment comprises administering a fluoropyrimidine.

15. The method of claim 14 in which the fluoropyrimidine is 5-fluorouracil (5-FU).

16. The method of claim 1, wherein the ratio is associated with a series of prognoses for a patient treated with 5-fluorouracil (5-FU).

* * * * *